(12) United States Patent
Iwata

(10) Patent No.: US 12,017,037 B2
(45) Date of Patent: Jun. 25, 2024

(54) STERILIZATION ADAPTOR

(71) Applicant: OLYMPUS CORPORATION, Tokyo (JP)

(72) Inventor: Kei Iwata, Tachikawa (JP)

(73) Assignee: OLYMPUS CORPORATION, Tokyo (JP)

(*) Notice: Subject to any disclaimer, the term of this patent is extended or adjusted under 35 U.S.C. 154(b) by 827 days.

(21) Appl. No.: 17/155,389

(22) Filed: Jan. 22, 2021

(65) Prior Publication Data

US 2021/0138226 A1 May 13, 2021

Related U.S. Application Data

(63) Continuation of application No. PCT/JP2019/007349, filed on Feb. 26, 2019.

(30) Foreign Application Priority Data

Jul. 26, 2018 (JP) .................................. 2018-140530

(51) Int. Cl.
*A61M 39/24* (2006.01)
*A61B 1/00* (2006.01)
*A61L 2/20* (2006.01)

(52) U.S. Cl.
CPC .......... *A61M 39/24* (2013.01); *A61B 1/00142* (2013.01); *A61L 2/20* (2013.01); *A61L 2202/14* (2013.01); *A61L 2202/24* (2013.01); *A61M 2039/2446* (2013.01)

(58) Field of Classification Search
CPC .......... A61M 39/24; A61M 2039/2446; A61B 1/00142; A61L 2/20; A61L 2202/14; A61L 2202/24

USPC ........................................................ 604/247
See application file for complete search history.

(56) References Cited

U.S. PATENT DOCUMENTS

2004/0096355 A1 5/2004 Ishibiki
2016/0302649 A1* 10/2016 Nakajima .......... A61B 1/00121

FOREIGN PATENT DOCUMENTS

| CA | 2 468 829 A1 | 6/2003 |
|----|----|----|
| EP | 1 452 186 A1 | 9/2004 |
| JP | S61-293417 A | 12/1986 |
| JP | H04-67445 B2 | 10/1992 |
| JP | H08-086966 A | 4/1996 |
| JP | 2000-157483 A | 6/2000 |
| JP | 2013-046701 A | 3/2013 |

(Continued)

OTHER PUBLICATIONS

International Search Report dated May 21, 2019 issued in PCT/JP2019/007349.

(Continued)

*Primary Examiner* — Phillip A Gray
(74) *Attorney, Agent, or Firm* — Scully, Scott, Murphy & Presser, P.C.

(57) ABSTRACT

A sterilization adaptor includes a check valve unit, a main body, and a vent valve unit. The check valve unit is disposed in the vent valve unit. The check valve unit includes a fluid passage. The vent valve unit includes a communication path. The vent valve unit includes a vent valve, a vent valve holding member, a rotation prevention member, and an elastic member. The main body includes an engaging portion configured to be engageable with a medical device by a biasing force of the elastic member.

2 Claims, 18 Drawing Sheets

(56) References Cited

FOREIGN PATENT DOCUMENTS

JP         2016-064050 A     4/2016
WO    WO 2015/194218 A1    12/2015

OTHER PUBLICATIONS

Extended European Search Report dated Mar. 7, 2022 received in PCT/JP2019/007349.

\* cited by examiner

STERILIZATION ADAPTOR

CROSS REFERENCE TO RELATED APPLICATION

This application is a continuation application of PCT/JP2019/007349 filed on Feb. 26, 2019, and claims benefit of Japanese Application No. 2018-140530 filed in Japan on Jul. 26, 2018, the entire contents of which are incorporated herein by this reference.

BACKGROUND OF THE INVENTION

1. Field of the Invention

The present invention relates to a sterilization adaptor configured to be attachable to and detachable from a medical device.

2. Description of the Related Art

Medical devices, such as endoscopes, need to be cleaned and disinfected by using a washer disinfector, since the medical devices will be reused after use.

In addition, there is a recent demand for performing not only the cleaning and disinfection process, but also an endoscope sterilization process to take measures against infectious diseases when the endoscope is used.

In general, in a gas sterilization process, first, in a conditioning step, the air in a chamber of a sterilization apparatus is removed, and the pressure in the chamber is brought close to a vacuum state.

After that, in a sterilization step, the endoscope sterilization process is carried out by pouring gas into the chamber, and then in a desorption step after completion of the sterilization process, the gas in the chamber is replaced with water vapor.

Lastly, in a drying/aeration step, the pressure in the chamber is restored to the atmospheric pressure by pouring air into the chamber.

In this case, in the gas sterilization process, the gas used in the sterilization step corrodes the components in the endoscope. Accordingly, there is a need to prevent the gas from entering into the endoscope.

However, if the inside of the endoscope is airtightly maintained in the gas sterilization process, there is a possibility that bending rubber of the endoscope is blown out when the pressure in the chamber, i.e., the pressure outside the endoscope is decreased to a negative pressure in the conditioning step.

In view of the above, a configuration in which an endoscope is provided with a vent pipe sleeve including a check valve unit for circulating gas from the inside of the endoscope to the outside of the endoscope is well known.

The check valve unit inhibits the circulation of gas from the outside of the endoscope to the inside of the endoscope, thereby preventing the gas from entering into the endoscope in the sterilization step.

Further, in a case where the pressure in the endoscope is higher than the pressure outside the endoscope, for example, when the inside of the chamber is close to the vacuum state and the inside of the endoscope is maintained in the atmospheric pressure state in the conditioning step, the check valve is opened due to a difference in pressure, thereby circulating the gas from the inside of the endoscope to the outside of the endoscope.

Accordingly, when the inside of the chamber is brought close to the vacuum state in the conditioning step, the pressure in the endoscope can be set to be equal to the pressure in the chamber, thereby making it possible to prevent the bending rubber from being blown out.

However, when the pressure in the chamber, i.e., the pressure outside the endoscope, is increased to the atmospheric pressure after the completion of the sterilization step, the pressure outside the endoscope is equal to the atmospheric pressure although the inside of the endoscope is close to the vacuum state.

Therefore, since the pressure in the endoscope is lower than the pressure outside the endoscope, the check valve unit is not opened and the bending rubber is crimped to a plurality of bending pieces. After the gas sterilization process, when the endoscope is taken out from the chamber and is used, the bending rubber is still crimped to the plurality of bending pieces. Accordingly, if a bending portion is bent, the bending rubber may bite into the bending pieces.

Accordingly, Japanese Patent Application Laid-Open Publication No. 2013-46701 discloses a configuration of an endoscope in which a vent pipe sleeve is provided with a check valve unit, as well as a vent valve unit for setting the pressure in the endoscope to be equal to the pressure outside the endoscope when a known sterilization adaptor to be attached to the vent pipe sleeve of the endoscope in the sterilization process is attached to or detached from the vent pipe sleeve.

SUMMARY OF THE INVENTION

A sterilization adaptor according to an aspect of the present invention is a sterilization adaptor configured to be attachable to and detachable from a medical device, the sterilization adaptor including: a check valve unit for inhibiting circulation of gas from an outside of the medical device to an inside of the medical device when the sterilization adaptor is attached to the medical device, and for circulating the gas from the inside to the outside; a main body including a hole; and a vent valve unit disposed in the hole, the vent valve unit causing the inside and the outside to communicate with each other through a gap formed between the vent valve unit and the main body and blocking the gap. The check valve unit is disposed in the vent valve unit, the check valve unit includes a fluid passage for circulating the gas, and the vent valve unit includes a communication path for causing the gap to communicate with the fluid passage. The vent valve unit includes: a vent valve in which the check valve unit is disposed, a vent valve holding member coupled to the vent valve and provided with the communication path, a rotation prevention member coupled to the vent valve holding member and configured to prevent rotation of the main body relative to the vent valve, and an elastic member disposed so as to couple the main body and the rotation prevention member and configured to bias the vent valve in a predetermined direction through the vent valve holding member and the rotation prevention member to block the gap. The main body includes an engaging portion configured to be engageable with the medical device by a biasing force of the elastic member.

Furthermore, a sterilization adaptor according to another aspect of the present invention is a sterilization adaptor configured to be attachable to and detachable from a medical device, the sterilization adaptor including: a check valve unit for inhibiting circulation of gas from an outside of the medical device to an inside of the medical device when the sterilization adaptor is attached to the medical device, and for circulating the gas from the inside to the outside; a main body including a hole; and a vent valve unit disposed in the hole, the vent valve unit causing the inside and the outside to communicate with each other through a gap formed between the vent valve unit and the main body and blocking the gap. The check valve unit is disposed in the vent valve unit, the check valve unit includes a fluid passage for circulating the gas, and the vent valve unit includes a communication path for causing the gap to communicate with the fluid passage. The vent valve unit includes: a vent valve in which the check valve unit is disposed; a vent valve holding member coupled to the vent valve and provided with the communication path; a rotation prevention member coupled to the vent valve holding member and configured to prevent rotation of the main body relative to the vent valve; and an elastic member disposed so as to couple the main body and the rotation prevention member and configured to bias the vent valve in a predetermined direction through the vent valve holding member and the rotation prevention member to block the gap. Blocking of the gap is released by moving the vent valve through the vent valve holding member by pressing the medical device against a biasing force of the elastic member.

DETAILED DESCRIPTION OF THE PREFERRED EMBODIMENTS

Figure 1:
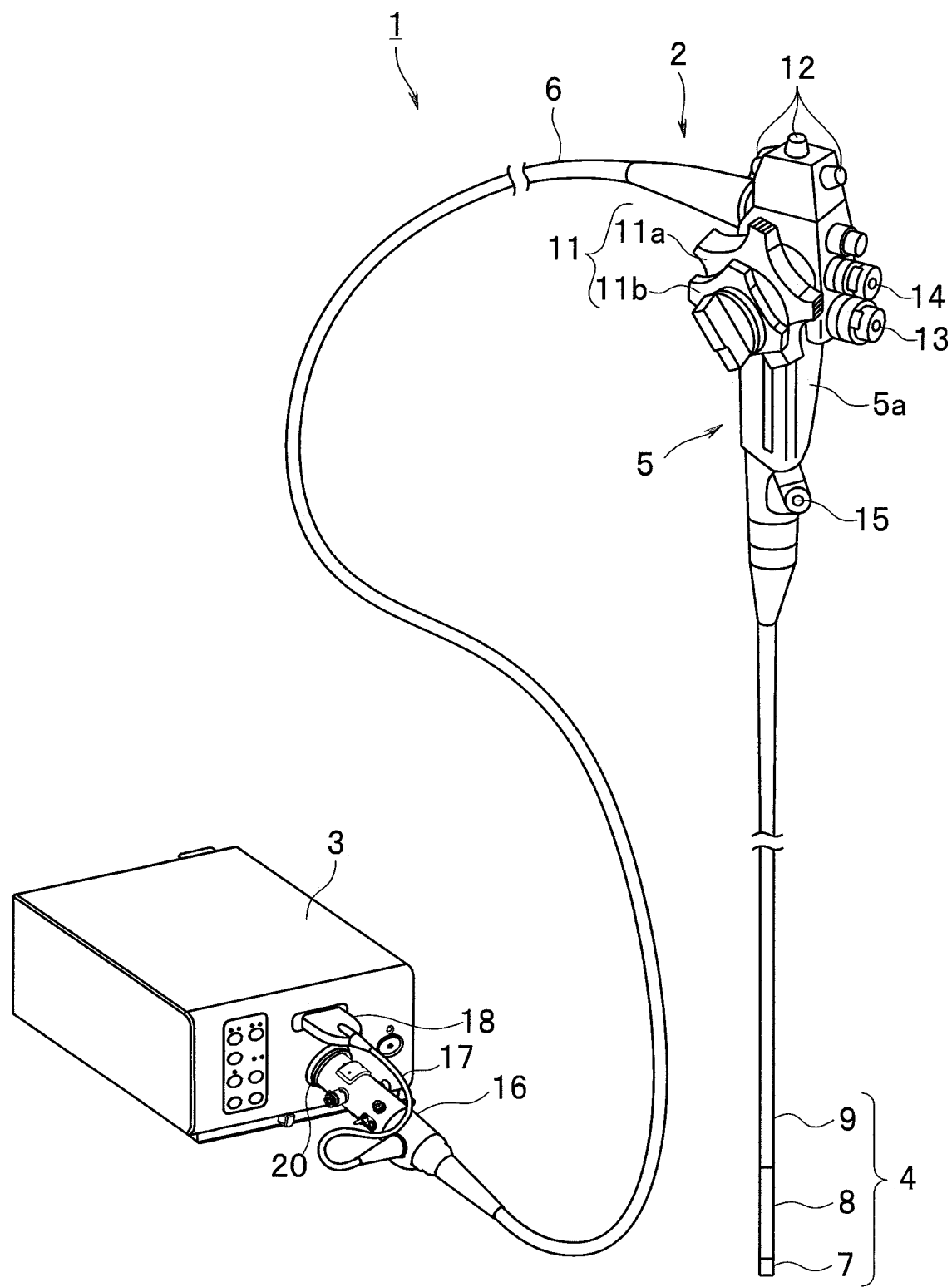
FIG. 1 is a perspective view illustrating an endoscope apparatus including an endoscope to and from which a sterilization adaptor according to a first embodiment is attachable and detachable.

Embodiments of the present invention will be described below with reference to the drawings. Note that in the drawings to be referred to in the following description, some components are illustrated with different scales so that the components can be illustrated with a size that can be recognized in the drawings. In other words, the present invention is not limited only to the number of components, the shape of each component, the ratio between the sizes of the components, and relative positional relationships among the components illustrated in the drawings.

Note that a medical device will be described below by taking an endoscope as an example.

First Embodiment

FIG. 1 is a perspective view of an endoscope apparatus including an endoscope to and from which a sterilization adaptor according to the present embodiment is attachable and detachable.

As illustrated in FIG. 1, an endoscope apparatus 1 includes a main part configured by an endoscope 2 and a camera control unit 3.

The endoscope 2 includes a main part configured by an insertion portion 4, an operation portion 5, a universal cable 6, and an endoscope connector 16.

The insertion portion 4 is an elongated long member to be inserted into an observation target section. The insertion portion 4 has a configuration in which a distal end portion 7, a bending portion 8, and a flexible tube portion 9 are connected to each other.

The operation portion 5 includes a grasping portion 5a. The grasping portion 5a is connected to a proximal end of the insertion portion 4. The operation portion 5 is provided with a bending operation portion 11, various switches 12, an air/water feeding button 13, a suction button 14, and the like.

The bending operation portion 11 includes, for example, vertical bending operation knob 11a and a horizontal bending operation knob 11b, which are used to perform a bending operation on the bending portion 8.

Examples of the switches 12 include a release switch, a freeze switch, and an observation mode selection switch for switching between normal observation and fluorescence observation.

Further, the operation portion 5 is provided with a treatment instrument insertion opening 15 through which a treatment instrument is inserted into or removed from a treatment instrument insertion conduit, not illustrated, provided in the insertion portion 4.

The universal cable 6 extends from a side portion of the operation portion 5. The endoscope connector 16 is provided at an extending end of the universal cable 6.

A signal transmission cable 17 extends from the endoscope connector 16, an electric connector 18 that is attachable to and detachable from the camera control unit 3 is provided at an end portion of the signal transmission cable 17.

Further, the endoscope connector 16 is provided with a vent pipe sleeve 20. Note that the vent pipe sleeve 20 may be provided on the operation portion 5.

Figure 2:
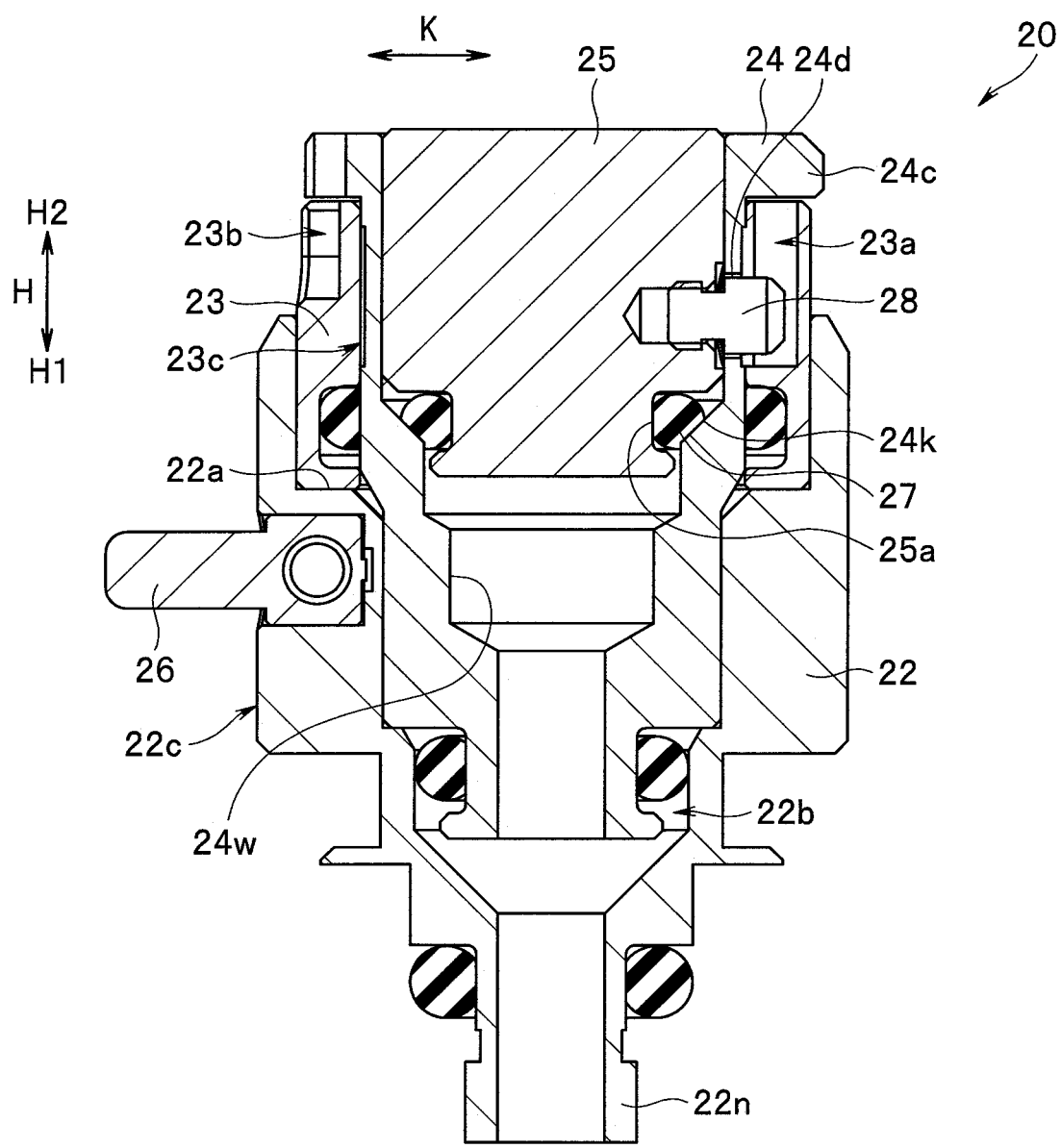
FIG. 2 is a sectional view illustrating a state where a vent pipe sleeve provided on an endoscope connector illustrated in FIG. 1 is closed.
Figure 3:
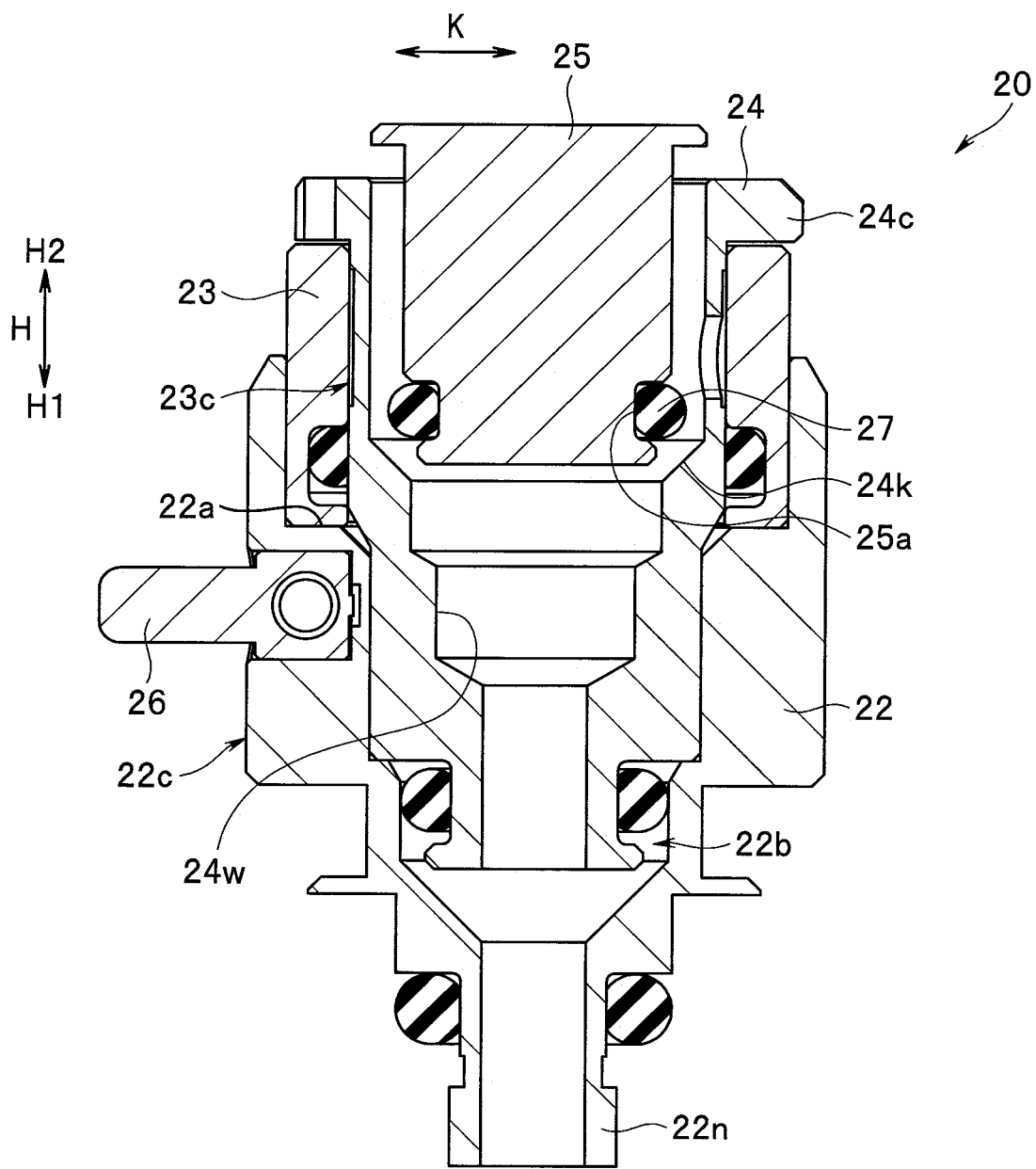
FIG. 3 is a sectional view illustrating a state where the vent pipe sleeve illustrated in FIG. 2 is opened.

Next, a configuration example of the vent pipe sleeve 20 will be described with reference to FIGS. 2 and 3. FIG. 2 is a sectional view illustrating a state where the vent pipe sleeve provided on the endoscope connector illustrated in FIG. 1 is closed. FIG. 3 is a sectional view of the vent pipe sleeve illustrated in FIG. 2 in a state where the vent pipe sleeve is opened.

As illustrated in FIG. 2, the vent pipe sleeve 20 includes a main part configured by a pipe sleeve main body 22 to be attached to the endoscope connector 16, a rotary ring 23, a sliding member 24, and a valve body 25 which are provided in the pipe sleeve main body 22.

The pipe sleeve main body 22 is composed of an elongated stepped pipe formed in a longitudinal axis direction H of the pipe sleeve main body 22, and a stepped through-hole 22b that allows the inside of the endoscope 2 to communicate with the outside is formed in the pipe sleeve main body 22. Further, a guide pin 26 protrudes from an outer peripheral surface 22c of the pipe sleeve main body 22.

Note that a screw 22n formed in a section on one end side H1 in the longitudinal axis direction H of the pipe sleeve main body 22 is screwed into a fixation member, not illustrated, provided in the endoscope connector 16, so that the pipe sleeve main body 22 is attached to the endoscope connector 16.

The rotary ring 23 is composed of an annular member and is rotatably disposed in a recessed portion 22a formed in a section on another end side H2 in the longitudinal axis direction H of the pipe sleeve main body 22.

A long hole 23a is formed on an outer peripheral surface of the rotary ring 23 along the longitudinal axis direction H.

The sliding member 24 is formed in an elongated pipe shape along the longitudinal axis direction H, and is disposed in a through-hole 23c of the rotary ring 23 and in the stepped through-hole 22b of the pipe sleeve main body 22. The section on the one end side H1 in the longitudinal axis direction H of the sliding member 24 is fixed to the stepped through-hole 22b with a screw. Further, a peripheral groove 24d having a cam shape is formed on an outer peripheral portion of the sliding member 24.

In other words, the sliding member 24 is integrally formed with the pipe sleeve main body 22. Further, a flange portion 24c is formed on the other end side H2 in the longitudinal axis direction H of the sliding member 24.

The sliding member 24 includes, inside thereof, a through-hole 24w that is formed along the longitudinal axis direction H and has a tapered surface 24k formed at a part of the sliding member 24 in the longitudinal axis direction H.

In the through-hole 24w, the valve body 25 is rotatably provided. A peripheral groove 25a is formed on an outer peripheral surface of the valve body 25 in the section on the one end side H1 in the longitudinal axis direction H, and a seal member 27, such as an O-shaped ring, is fitted into the peripheral groove 25a.

As illustrated in FIG. 2, the seal member 27 comes into close contact with the tapered surface 24k, thereby maintaining water-tightness between the sliding member 24 and the valve body 25.

Further, a screw hole is formed on the outer peripheral surface of the valve body 25 in the section on the other end side H2 in the longitudinal axis direction H, and a cam receiving pin 28 is screwed into the screw hole and is attached thereto.

The cam receiving pin 28 protrudes to the outside in a radial direction K of the vent pipe sleeve 20 through the peripheral groove 24d formed on the sliding member 24, and a head portion of the cam receiving pin is fitted into the above-described long hole 23a.

Note that the head portion of the cam receiving pin 28 is fitted into the long hole 23a, thereby positioning the valve body 25 in the longitudinal axis direction H with respect to the sliding member 24.

A sterilization adaptor 29 (see FIG. 4) is attached to the vent pipe sleeve 20 configured as described above, and a cam pin 44 (see FIG. 4) to be described below is fitted into a peripheral groove 23b of the rotary ring 23. When the sterilization adaptor 29 is rotated, the cam receiving pin 28 that is fitted into the peripheral groove 24d having a cam shape is rotated along the cam shape.

As a result, the valve body 25 is moved to a position illustrated in FIG. 3 along the longitudinal axis direction H.

Note that when the valve body 25 is moved to the position illustrated in FIG. 3, the seal member 27 is spaced apart from the tapered surface 24k.

With this configuration, the water-tightness between the valve body 25 and the sliding member 24 is released and the vent pipe sleeve 20 is opened, thereby causing the inside and outside of the endoscope 2 to communicate with each other through the through-hole 24w.

Note that the configuration of the vent pipe sleeve 20 described above is merely an example and is not limited to the above-described configuration.

For example, although not illustrated, a known check valve unit may be provided in the valve body 25.

Further, the vent pipe sleeve 20 may have a structure in which the valve body 25 is omitted and the vent pipe sleeve is opened during the sterilization process and can be sealed with a cap or the like during the cleaning and disinfection process.

Next, the configuration of the sterilization adaptor that is attachable to and detachable from the vent pipe sleeve 20 will be described with reference to FIGS. 4 to 10.

Figure 4:
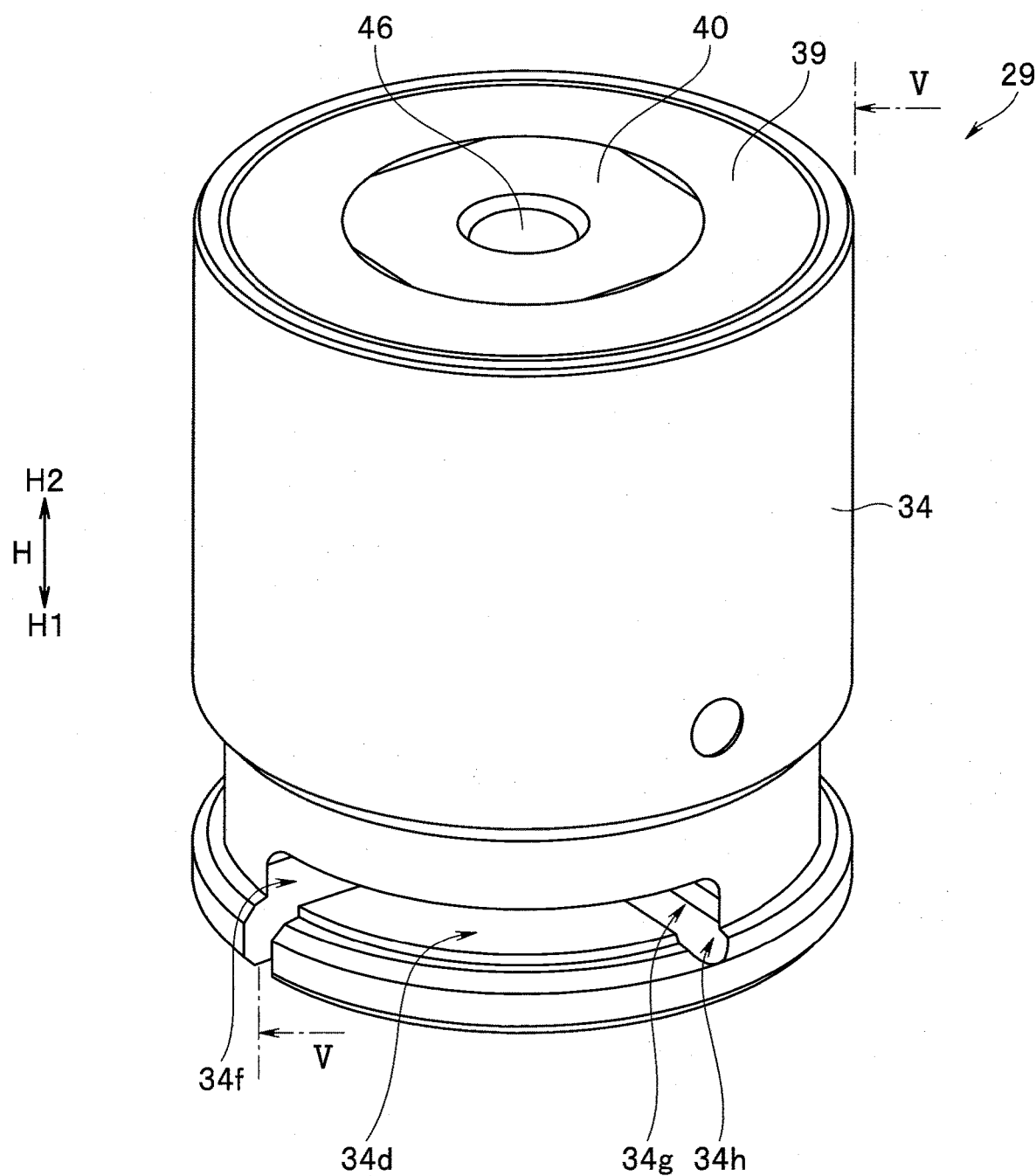
FIG. 4 is a perspective view of the sterilization adaptor that is attachable to and detachable from the vent pipe sleeve illustrated in FIG. 2.
Figure 5:
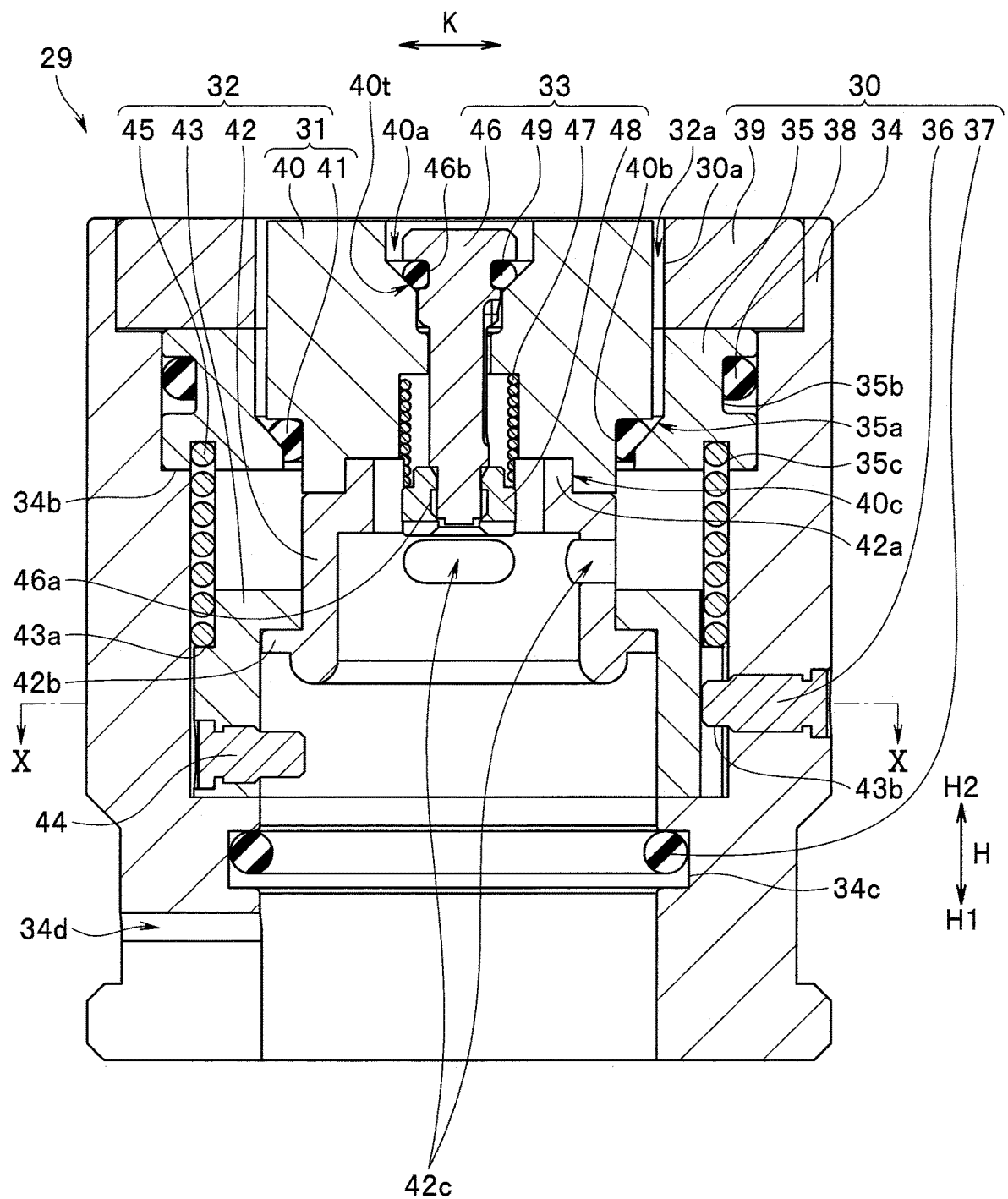
FIG. 5 is a sectional view of the sterilization adaptor taken along a line V-V in FIG. 4.

FIG. 4 is a perspective view of the sterilization adaptor that is attachable to and detachable from the vent pipe sleeve illustrated in FIG. 2. FIG. 5 is a sectional view of the sterilization adaptor taken along the line V-V in FIG. 4.

Figure 6:
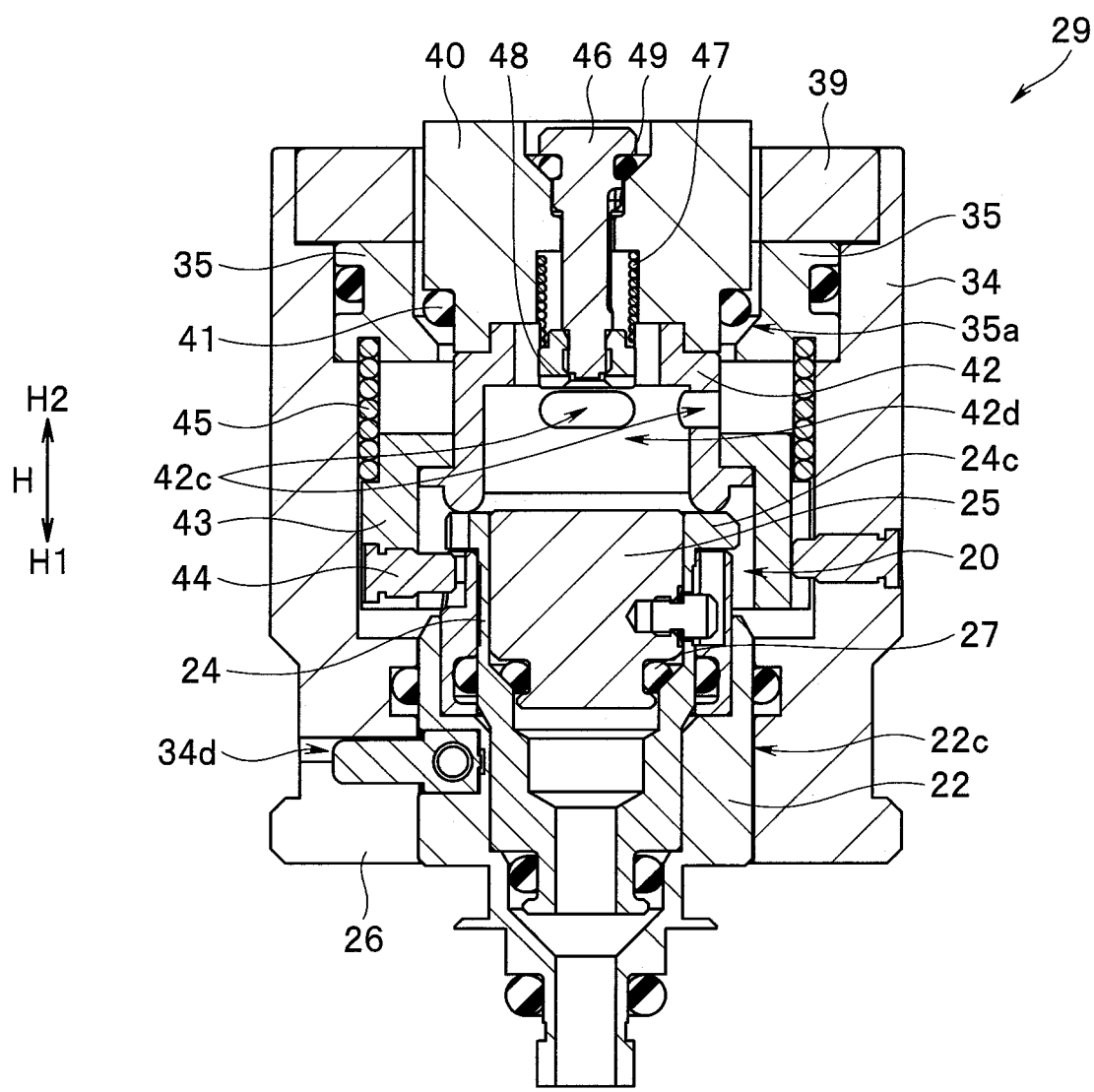
FIG. 6 is a sectional view illustrating a state where the sterilization adaptor illustrated in FIG. 4 is attached to the vent pipe sleeve illustrated in FIG. 2 and a guide pin illustrated in FIG. 2 is fitted into a first position of a guide groove formed in the sterilization adaptor illustrated in FIG. 4.

Further, FIG. 6 is a sectional view illustrating a state where the sterilization adaptor illustrated in FIG. 4 is attached to the vent pipe sleeve illustrated in FIG. 2 and the guide pin illustrated in FIG. 2 is fitted into a first position of the guide groove formed in the sterilization adaptor illustrated in FIG. 4.

Figure 7:
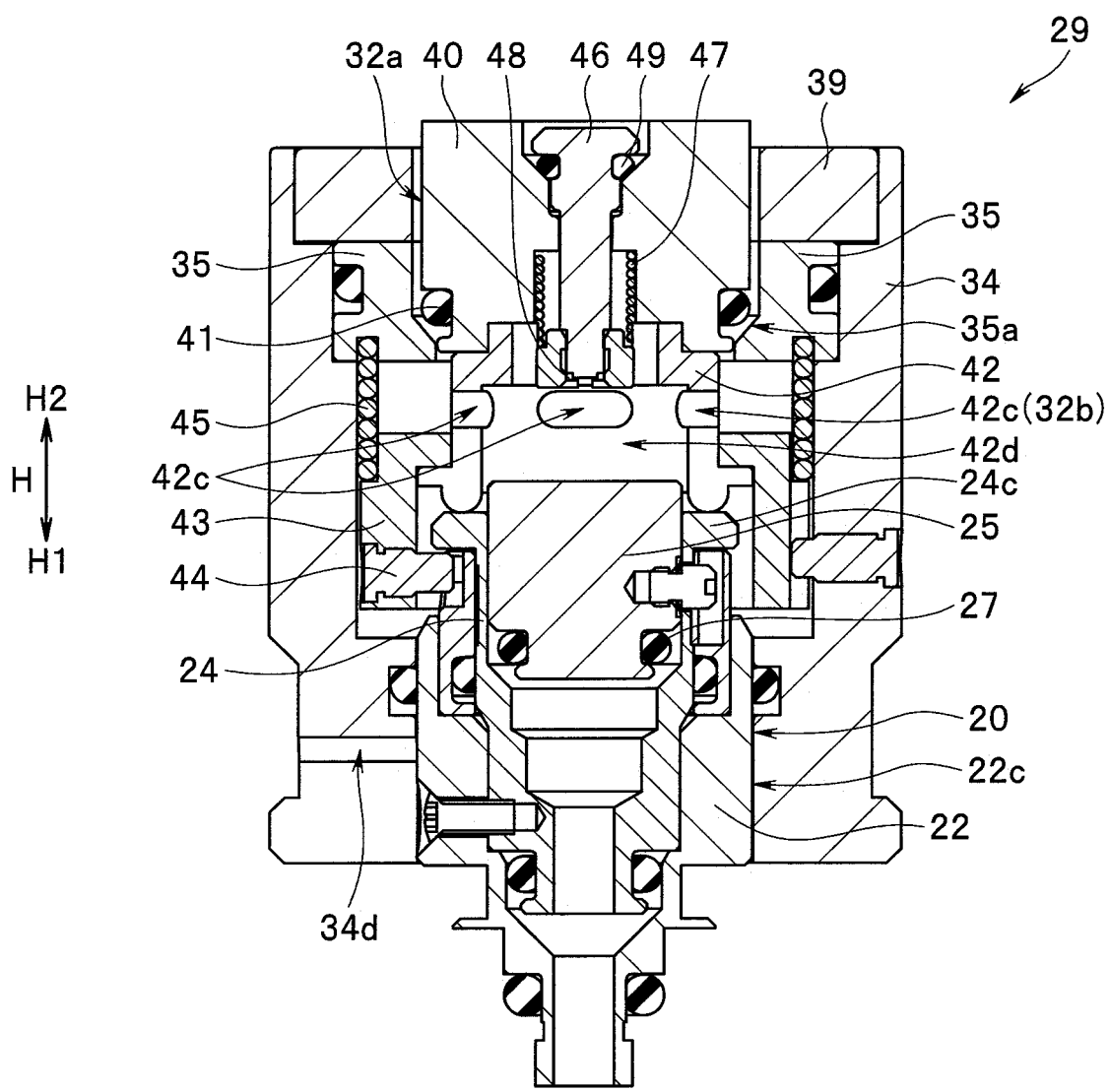
FIG. 7 is a sectional view of the vent pipe sleeve and the sterilization adaptor in a direction different by 90° from the section of the vent pipe sleeve illustrated in FIG. 2, and illustrates a state where the guide pin illustrated in FIG. 2 is moved to a second position of the guide groove.
Figure 8:
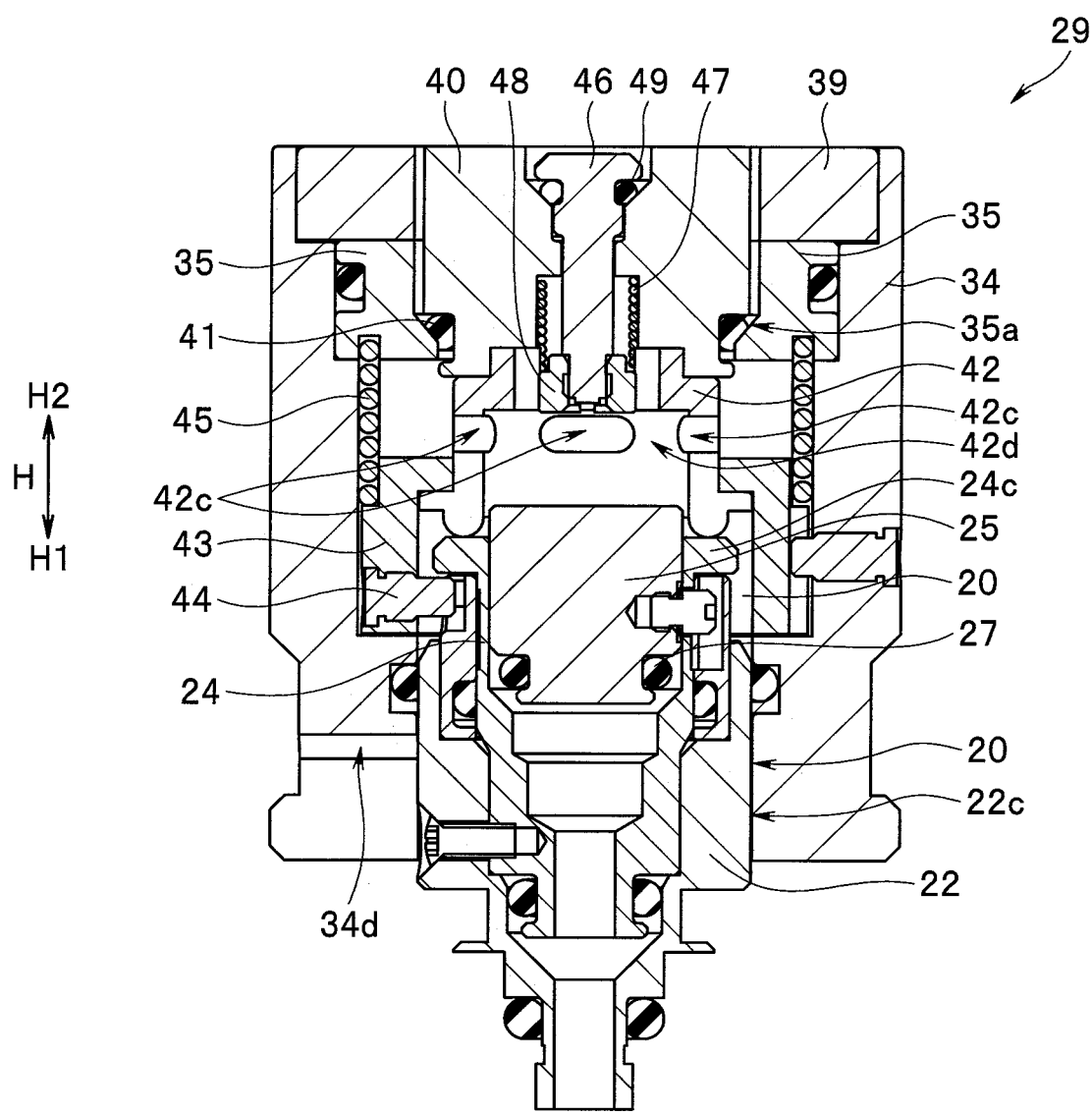
FIG. 8 is a sectional view of the vent pipe sleeve and the sterilization adaptor in a direction different by 90° from the section of the vent pipe sleeve illustrated in FIG. 2, and illustrates a state where the guide pin illustrated in FIG. 2 is moved to a third position of the guide groove and a check valve unit is closed.

FIG. 7 is a sectional view of the vent pipe sleeve and the sterilization adaptor in a direction different by 90° from the section of the vent pipe sleeve illustrated in FIG. 2, and illustrates the state where the guide pin illustrated in FIG. 2 is moved to a second position of the guide groove. FIG. 8 is a sectional view of the vent pipe sleeve and the sterilization adaptor in a direction different by 90° from the section of the vent pipe sleeve illustrated in FIG. 2, and illustrates the state where the guide pin illustrated in FIG. 2 is moved to a third position of the guide groove and the check valve unit is closed.

Figure 9:
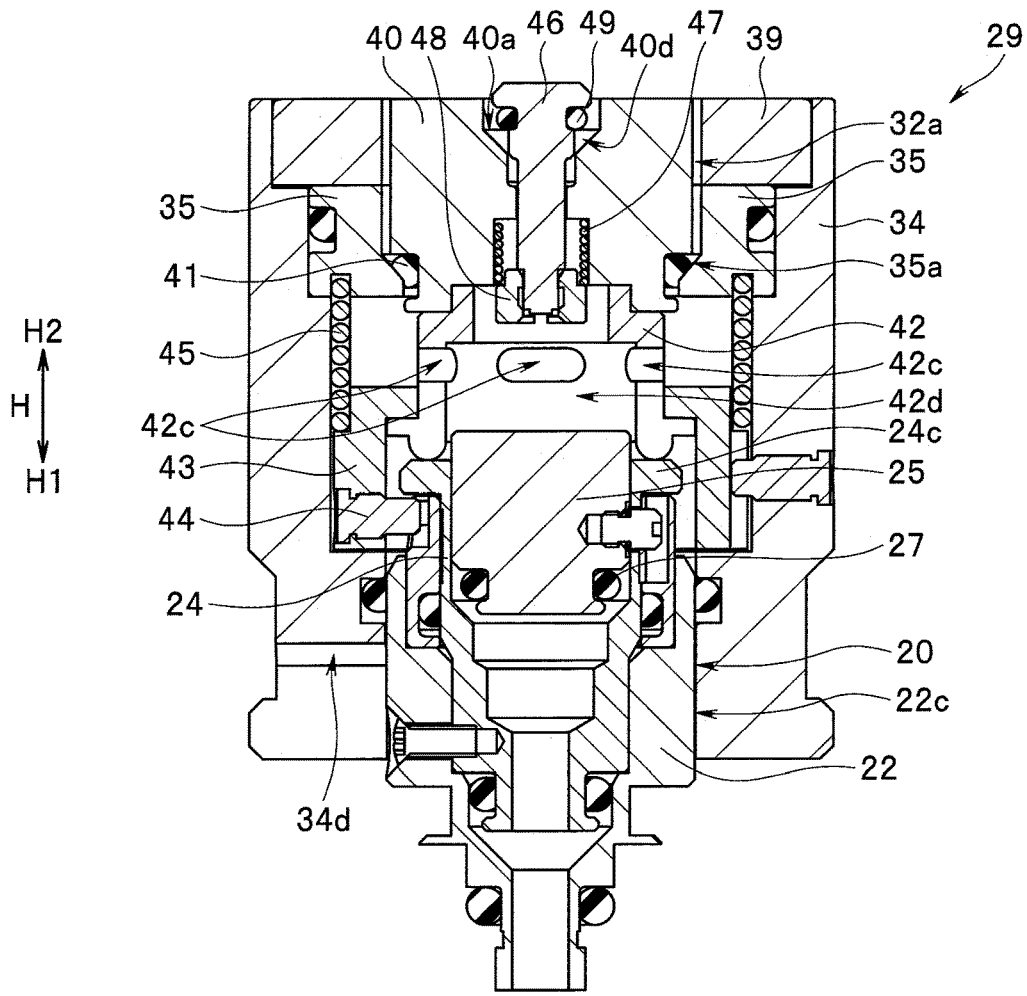
FIG. 9 is a sectional view of the vent pipe sleeve and the sterilization adaptor in a state where the check valve unit illustrated in FIG. 8 is opened.
Figure 10:
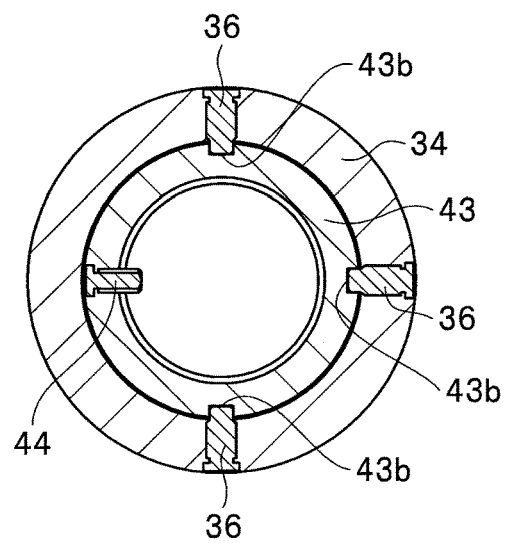
FIG. 10 is a sectional view of the sterilization adaptor taken along a line X-X in FIG. 5.

FIG. 9 is a sectional view of the vent pipe sleeve and the sterilization adaptor in a state where the check valve unit illustrated in FIG. 8 is opened. FIG. 10 is a sectional view of the sterilization adaptor taken along the line X-X in FIG. 5.

As illustrated in FIG. 5, the sterilization adaptor 29 includes a main part configured by a main body 30 including a hole 30a along the longitudinal axis direction, a vent valve unit 32 disposed in the hole 30a of the main body 30, and a check valve unit 33 disposed in the vent valve unit 32. As illustrated in FIGS. 2, 3, and 6 to 9, the sterilization adaptor 29 is attachable to and detachable from the vent pipe sleeve 20.

The main body 30 includes a main part configured by a main body member 34, a spring pressing member 35, engaging pins 36, a first seal member 37, a second seal member 38, and a retaining ring 39.

The main body member 34 is formed of a cylindrical member in which a through-hole is formed in a stepped shape along the longitudinal axis direction H.

Further, as illustrated in FIGS. 4 and 5, the main body member 34 is provided with a guide groove 34d as an engaging portion on the outer peripheral surface in the section on the one end side H1 in the longitudinal axis direction H.

When the sterilization adaptor 29 is attached to the vent pipe sleeve 20, the guide pin 26 of the vent pipe sleeve 20 is inserted into the guide groove 34d, thereby enabling engagement by a spring member 45 to be described below.

Further, the main body member 34 is provided with a groove 34c formed on an inner peripheral surface which is formed by a through-hole in the section on the one end side H1 in the longitudinal axis direction H. Further, the first seal member 37, which is formed of, for example, an O-shaped ring, is disposed in the groove 34c.

When the sterilization adaptor 29 is attached to the vent pipe sleeve 20, as illustrated in FIGS. 6 to 9, the first seal member 37 contacts the outer peripheral surface 22c of the pipe sleeve main body 22. With this configuration, the water-tightness between the vent pipe sleeve 20 and the main body 30 is maintained.

The spring pressing member 35 is formed of a ring-shaped member having a tapered surface 35a in the section on the one end side H1 in the longitudinal axis direction H.

Further, the spring pressing member 35 is disposed on a bottom surface 34b of the recessed portion formed in the section on the other end side H2 in the longitudinal axis direction H in the through-hole of the main body member 34.

Further, a groove 35b is formed on the outer peripheral surface of the spring pressing member 35, and the second seal member 38, which is formed of, for example, an O-shaped ring, is disposed in the groove 35b in a state where the second seal member 38 contacts the inner peripheral surface of the main body member 34. With this configuration, the water-tightness between the main body member 34 and the spring pressing member 35 is maintained.

In the recessed portion of the through-hole of the main body member 34, in the section on the other end side H2 in the longitudinal axis direction H of the spring pressing member 35, the retaining ring 39 of the ring-shaped member, which includes on the outer peripheral surface thereof a male screw portion not illustrated, is screwed and fixed into a female screw portion which is formed in the inner peripheral surface of the main body member 34. With this configuration, the retaining ring 39 regulates the movement of the spring pressing member 35 in the longitudinal axis direction H.

In the main body 30, the hole 30a described above is formed in the inner peripheral surface of each of the spring pressing member 35 and the retaining ring 39.

A vent valve 31 to be described below is provided in the hole 30a. In the hole 30a, a gap 32a, which causes the inside and the outside of the sterilization adaptor 29 communicate with each other, is formed between the inner peripheral surface of each of the spring pressing member 35 and the retaining ring 39 and a vent valve body 40, which is described below, of the vent valve 31.

The vent valve unit 32 includes a main part configured by the vent valve 31, a rotation prevention member 43, the spring member 45 as an elastic member, and a valve body holding member 42 as a vent valve holding member. The vent valve 31 is formed of the vent valve body 40 and a seal member 41.

The vent valve body 40 is formed of a cylindrical member including a stepped through-hole 40a as a fluid channel for circulating gas in the vent valve body along the longitudinal axis direction H.

Further, in the vent valve body 40, the seal member 41, which is formed of, for example, an O-shaped ring, is disposed in a peripheral groove 40b formed on the outer peripheral surface in the section on the one end side H1 in the longitudinal axis direction H.

Further, a screw hole 40c is formed in the inner peripheral surface of the vent valve body 40 in the section on the one end side H1 in the longitudinal axis direction H.

The valve body holding member 42 is formed of a stepped cylindrical member, a protruding portion 42a provided with a male screw is formed on the outer peripheral surface in the section on the other end side H2 in the longitudinal axis direction H, and a flange portion 42b is formed on the outer peripheral surface in the section on the one end side H1 in the longitudinal axis direction H.

The valve body holding member 42 is fixed to the vent valve body 40 by the protruding portion 42a being screwed into the screw hole 40c of the vent valve body 40.

Further, the valve body holding member 42 is provided with a plurality of through-holes 42c as communication paths for causing a space 42d to communicate with the gap 32a described above. Note that the through-holes 42c also communicates with the through-hole 40a.

The rotation prevention member 43 is formed of a stepped cylindrical member, and includes an inward flange which is formed in the section on the other end side H2 in the longitudinal axis direction H. The flange portion 42b of the valve body holding member 42 is in contact with and is fixed by bonding to a surface of the inward flange, the surface of the inward flange being located in the section on the one end side H1 in the longitudinal axis direction H. With this configuration, the rotation prevention member 43 prevents relative rotation between the main body 30 and the vent valve 31.

Further, a step 43a is formed on the outer peripheral surface in the section on the other end side H2 in the longitudinal axis direction H of the rotation prevention member 43.

Further, the spring member 45 is disposed along the longitudinal axis direction H in a state where the spring member 45 is contracted between the step 43a and grooves 35c formed on the surface of the spring pressing member 35 in the section on the one end side H1 in the longitudinal axis direction H.

Further, in the rotation prevention member 43, the cam pin 44 is disposed in the through-hole formed in the radial direction K such that a distal end of the cam pin protrudes toward the inside of the rotation prevention member 43.

Further, as illustrated in FIG. 10, on the outer peripheral surface of the rotation prevention member 43, grooves 43b into which distal end portions of the engaging pins 36 each protruding from the main body 30 toward the inside in the radial direction K are respectively fitted are formed along the longitudinal axis direction H.

Note that a plurality of grooves 43b, for example, three grooves, are formed along the peripheral direction of the rotation prevention member 43. That is, also three engaging pins 36 to be fitted into the grooves 43b are provided.

With this configuration, the rotation prevention member 43 is moved separately from the main body member 34 in the longitudinal axis direction H, and is moved in the same direction as the main body member 34 in the rotation direction.

Note that the number of the grooves 43b formed in the rotation prevention member 43 and the number of the engaging pins 36 are not limited to three, but instead may be one, two, or four or more.

In a state where no pressure is applied to the main body 30 and the valve body holding member 42, the rotation prevention member 43 is biased to the one end side H1 in the longitudinal axis direction H by a biasing force of the spring member 45 to the one end side H1 in the longitudinal axis direction H.

As a result, the valve body holding member 42 and the vent valve body 40, which are fixed to the rotation prevention member 43, are also biased to the one end side H1 in the longitudinal axis direction H. Accordingly, the seal member 41 is pressed against the tapered surface 35a formed on the inner peripheral surface of the spring pressing member 35.

Accordingly, the gap 32a is blocked, thereby maintaining the water-tightness between the spring pressing member 35 and the vent valve body 40.

The check valve unit 33 is provided in the through-hole 40a of the vent valve body 40.

Further, the check valve unit 33 inhibits circulation of gas from the outside to the inside of the endoscope 2 through the through-hole 40a, and allows gas to circulate from the inside to the outside of the endoscope 2 when the pressure in the endoscope 2 is higher than the pressure outside the endoscope 2.

Further, the check valve unit 33 includes a main part configured by a shaft body 46, a spring member 47, a seal member 49, and a spring presser 48.

The shaft body 46 is slidably provided along the longitudinal axis direction H within the through-hole 40a.

A male screw portion 46a is formed on the outer peripheral surface of the shaft body 46 in the section on the one end side H1 in the longitudinal axis direction H, and the spring presser 48 is screwed into the male screw portion 46a.

The spring member 47 is disposed in the longitudinal axis direction H, with the spring member being contracted between the spring presser 48 and a recessed portion formed in the section on the one end side H1 in the longitudinal axis direction H in the vent valve body 40.

Further, the seal member 49, which is formed of, for example, an O-shaped ring, is disposed in an annular groove 46b formed on the outer peripheral surface of the shaft body 46 in the section on the other end side H2 in the longitudinal axis direction H.

The seal member 49 contacts and is pressed against a tapered surface 40t, which is formed at the through-hole 40a in the vent valve body 40, when the spring presser 48 and the shaft body 46 are biased to the one end side H1 in the longitudinal axis direction by a biasing force of the spring member 47 to the one end side H1 in the longitudinal axis direction H.

With this configuration, the through-hole 40a serving as a gas channel is blocked, thereby maintaining air-tightness between the vent valve body 40 and the shaft body 46.

Next, operations according to the present embodiment will be described with reference to FIGS. 4 and 6 to 9.

When an operator attaches the sterilization adaptor 29 to the vent pipe sleeve 20, the operator grips the main body member 34 of the sterilization adaptor 29.

Next, as illustrated in FIGS. 4 and 6, the guide pin 26 of the vent pipe sleeve 20 is inserted into the guide groove 34d along the longitudinal axis direction H until the guide pin 26 contacts the guide groove 34d at a first position 34f of the guide groove 34d formed in the main body member 34, against the biasing force of the spring member 45 toward the one end side H1 in the longitudinal axis direction H. In this case, the cam pin 44 is fitted into the peripheral groove 23b of the rotary ring 23.

In this case, as illustrated in FIG. 6, the flange portion 24c of the sliding member 24 lifts the valve body holding member 42 toward the other end side H2 in the longitudinal axis direction H, against the biasing force of the spring member 45 to the one end side H1 in the longitudinal axis direction H.

As a result, the vent valve body 40 is also moved toward the one end side H1 in the longitudinal axis direction H, so that the seal member 41 is spaced apart from the tapered surface 35a.

Accordingly, the gap 32a and the through-holes 42c communicate with each other. In other words, the vent valve body 40 is opened. In this case, the vent pipe sleeve 20 is in the closed state, and thus the inside and the outside of the endoscope 2 do not communicate with each other.

After that, the operator rotates the main body member 34 in the peripheral direction until the guide pin 26 is guided to a second position 34g of the guide groove 34d, as illustrated in FIG. 4, while keeping the state against the biasing force of the spring member 45 toward the one end side H1 along the longitudinal axis direction H.

As a result, the cam receiving pin 28 fitted into the long hole 23a is rotated along the cam shape formed on the sliding member 24, so that the valve body 25 is moved from the position illustrated in FIG. 2 to the position illustrated in FIG. 3 along the longitudinal axis direction H.

Accordingly, the seal member 27 is spaced apart from the tapered surface 24k of the sliding member 24, so that the vent pipe sleeve 20 is opened.

With this configuration, the inside of the endoscope 2 communicates with the space 42d of the valve body holding member 42, and the through-holes 42c communicates with the outside of the endoscope 2 through the gap 32a.

Note that in this case, the movement of the cam pin 44 in the longitudinal axis direction H is regulated by the flange portion 24c of the sliding member 24.

After that, when the operator releases the grip of the main body member 34, as illustrated in FIGS. 4, 8, and 9, the main body 30 is moved to the other end side H2 in the longitudinal axis direction H until the guide pin 26 contacts the guide groove 34d at a third position 34h of the guide groove 34d by the biasing force of the spring member 45 to the one end side H1 in the longitudinal axis direction H.

In this case, as described above, the seal member 41 is pressed against the tapered surface 35a of the spring pressing member 35 by the spring member 45, so that the gap 32a is blocked and the inside of the endoscope 2 is blocked from the outside. In other words, the vent valve body 40 is closed.

As a result, the sterilization adaptor 29 is attached to the vent pipe sleeve 20. In this state, the endoscope 2 is put in a gas sterilization apparatus.

Note that in the process in which the sterilization adaptor 29 is attached to the vent pipe sleeve 20, as illustrated in FIGS. 6 to 8, the check valve unit 33 is in the closed state. In other words, the through-hole 40a is in the blocked state.

Further, in a state where the sterilization adaptor 29 is attached to the vent pipe sleeve 20 illustrated in FIGS. 8 and 9, the guide pin 26 engages with the guide groove 34d that is formed at a depth where the cam pin can be easily hooked. This configuration prevents the sterilization adaptor 29 from being rotated and detached during the sterilization process.

After that, when the sterilization process is performed on the endoscope 2 in the gas sterilization apparatus, first, in the above-described conditioning step, the pressure in the sterilization apparatus is decreased to be brought close to the vacuum state.

In this case, as illustrated in FIG. 8 described above, the check valve unit 33 and the vent valve body 40 are in the closed state even when the vent pipe sleeve 20 is opened. Accordingly, the inside of the endoscope 2 and the inside of the sterilization apparatus do not communicate with each other. Therefore, the pressure in the endoscope 2 becomes higher than the pressure in the sterilization apparatus.

As a result, as illustrated in FIG. 9, the shaft body 46 and the spring presser 48 are automatically lifted toward the other end side H2 in the longitudinal axis direction H against the biasing force of the spring member 47 toward the one end side H1 in the longitudinal axis direction H, due to a difference in pressure, so that the seal member 49 is spaced apart from the tapered surface 40t. In other words, the check valve unit 33 is opened.

Accordingly, a fluid passage 40d that causes the inside and the outside of the sterilization adaptor 29 to communicate with each other is formed between the vent valve body 40 and the shaft body 46.

After that, the inside of the endoscope 2 communicates with the inside of the sterilization apparatus through the gap between the sliding member 24 and the valve body 25, the space 42d in the sterilization adaptor 29, and the fluid passage 40d, from the inside of the endoscope 2.

With this configuration, the pressure in the endoscope 2 is not higher than, that is, is equal to the pressure in the sterilization apparatus in the conditioning step. Accordingly, as described above, the bending rubber constituting the bending portion 8 can be prevented from being blown out.

After that, when gas is continuously discharged from the inside of the endoscope 2 into the sterilization apparatus and the difference between the pressure in the endoscope 2 and the pressure in the sterilization apparatus is lower than a prescribed pressure difference, as illustrated in FIG. 8, the fluid passage 40d is automatically blocked due to the difference in pressure, so that the inside of the endoscope 2 and the inside of the sterilization apparatus are blocked from each other.

Accordingly, during the sterilization step, the inside of the endoscope 2 and the inside of the sterilization apparatus are blocked from each other and thus sterilization gas is not introduced into the endoscope 2, thereby making it possible to prevent deterioration of internal members of the endoscope due to the gas.

After the completion of the sterilization step, when the endoscope 2 in the state where the sterilization adaptor 29 as illustrated in FIG. 8 is attached to the vent pipe sleeve 20 is taken out from the sterilization apparatus, the inside of the endoscope 2 is blocked from outside. Accordingly, the pressure in the endoscope 2 is lower than the atmospheric pressure and the bending rubber constituting the bending portion 8 is crimped to a plurality of bending pieces.

After that, the operator detaches the sterilization adaptor 29 from the vent pipe sleeve 20. First, the operator grips the main body 30 and depresses the main body 30 against the biasing force of the spring member 45 toward the one end side H1 in the longitudinal axis direction H so that the state is shifted from the state illustrated in FIG. 8 to the state illustrated in FIG. 7.

As a result, when the flange portion 24c of the sliding member 24 contacts the valve body holding member 42 and the main body 30 is depressed until the guide pin 26 is guided to a second position 24g of the guide groove 34d as illustrated in FIG. 7, the seal member 41 is spaced apart from the tapered surface 35a against the biasing force of the spring member 45 toward the one end side H1 in the longitudinal axis direction H, as described above.

In this case, a communication path 32b is formed by the through-holes 42c formed around the valve body holding member 42, and the gap 32a communicates with the space 42d in the main body 30, so that the gap 32a and the space 42d communicate with each other. In other words, the vent valve body 40 is opened.

In this case, air enters into the endoscope 2 through the gap 32a, the communication path 32b, the space 42d, and the gap between the sliding member 24 and the valve body 25, so that the difference between the pressure in the endoscope 2 and the atmospheric pressure decreases.

Accordingly, it is possible to prevent the bending rubber constituting the bending portion 8 from biting into the plurality of bending pieces and being damaged when the bending portion 8 is used in a state where the bending rubber is crimped to the plurality of bending pieces.

After that, the operator grips the main body member 34 and rotates the main body member 34 in a direction opposite to that at the time of the attachment, and moves the guide pin 26 to the first position 34f illustrated in FIG. 6 from the second position 34g illustrated in FIG. 7.

As a result, the valve body 25 is moved from the state illustrated in FIG. 3 to the state illustrated in FIG. 2 by the rotary ring 23 being rotated in the direction opposite to that described above, and the seal member 27 is brought into contact with the tapered surface 24k, and thereby the vent pipe sleeve 20 is closed.

After that, the main body member 34 is drawn out toward the other end side H2 in the longitudinal axis direction H, thereby detaching the guide pin 26 from the guide groove 34d. As a result, the sterilization adaptor 29 is removed from the vent pipe sleeve 20.

Thus, the configuration of the sterilization adaptor 29 according to the present embodiment prevents the bending rubber constituting the bending portion 8 from being crimped to the plurality of bending pieces when the sterilization adaptor 29 is removed from the vent pipe sleeve 20 after the sterilization process.

Further, the communication path 32b allows the gap 32a and the fluid passage 40d to communicate with each other, which eliminates the need for separately providing two channels, i.e., a channel leading to the inside of the endoscope 2 from the vent valve unit 32 and a channel leading to the inside of the endoscope 2 from the check valve unit 33. Consequently, downsizing of the sterilization adaptor 29 is achieved.

Further, until the sliding member 24 of the vent pipe sleeve 20 is moved to the one end side H1 in the longitudinal axis direction H and the seal member 27 abuts against the tapered surface 24k, that is, during a period in which the vent pipe sleeve is opened, the seal member 41 is constantly spaced apart from the tapered surface 35a. Therefore, it is possible to efficiently replace air between the inside and the outside of the endoscope 2.

Further, in the case of removing the sterilization adaptor 29, the vent pipe sleeve 20 is reliably closed, thereby making it possible to prevent medicinal solution from entering into the endoscope 2 during the cleaning and disinfection process.

In addition, in the case of attaching or detaching of the sterilization adaptor 29, the main body member 34 and the valve body holding member 42 are rotated together, as described above.

Thus, it is possible to prevent the seal member 41 from being worn by a frictional force in the rotation direction to be repeatedly applied to the seal member 41 by the main body member and the valve body holding member being rotated separately.

Further, if the main body member 34 and the valve body holding member 42 are rotated separately, a force in the rotation direction is applied to the spring member 45 when attaching and detaching the sterilization adaptor. However, like in the present embodiment, if the main body member 34 and the valve body holding member 42 are rotated together, the force to be applied to the spring member can be reduced. Accordingly, even when the attachment and detachment are repeated, the spring member 45 and the seal member 41 are less likely to deteriorate and thus it is possible to prevent a failure from occurring in the sterilization adaptor 29.

Further, there is no need to provide the endoscope 2 with a new vent valve, thereby preventing an increase in the size of the endoscope 2 itself.

Therefore, like in the conventional one, the sterilization adaptor 29 can be detached from the vent pipe sleeve 20 without causing any problem and the endoscope 2 can be put into the cleaning and disinfection apparatus to perform the cleaning and disinfection process.

In addition, the check valve unit 33 is disposed in the vent valve unit 32, thereby reducing the size of the sterilization adaptor 29 in the longitudinal axis direction H, as compared with a configuration in which the check valve unit 33 is disposed on the other end side H2 in the longitudinal axis direction H with respect to the vent valve unit 32.

In other words, even if the check valve unit 33 and the vent valve unit 32 are provided, the sterilization adaptor 29 can be downsized.

Accordingly, it is possible to prevent a situation where the endoscope 2 cannot be put into a sterilization bag, with the sterilization adaptor 29 being attached to the vent pipe sleeve 20 when the sterilization process is performed.

Further, the sterilization adaptor 29 including the vent valve unit 32 and the check valve unit 33 like in the present embodiment described above can be applied to various endoscopes provided with the vent pipe sleeve 20, and thus the gas sterilization process can be performed on various types of endoscopes.

Note that the configuration according to the present embodiment can also be applied to a configuration in which a vent valve is provided on a side of the vent pipe sleeve 20.

As described above, it is possible to provide the downsized sterilization adaptor 29 capable of preventing gas from entering into the endoscope 2 in the sterilization process and setting the pressure in the endoscope 2 to be equal to the pressure outside the endoscope 2 in the attachment to or detachment from the endoscope 2.

Second Embodiment

Figure 11:
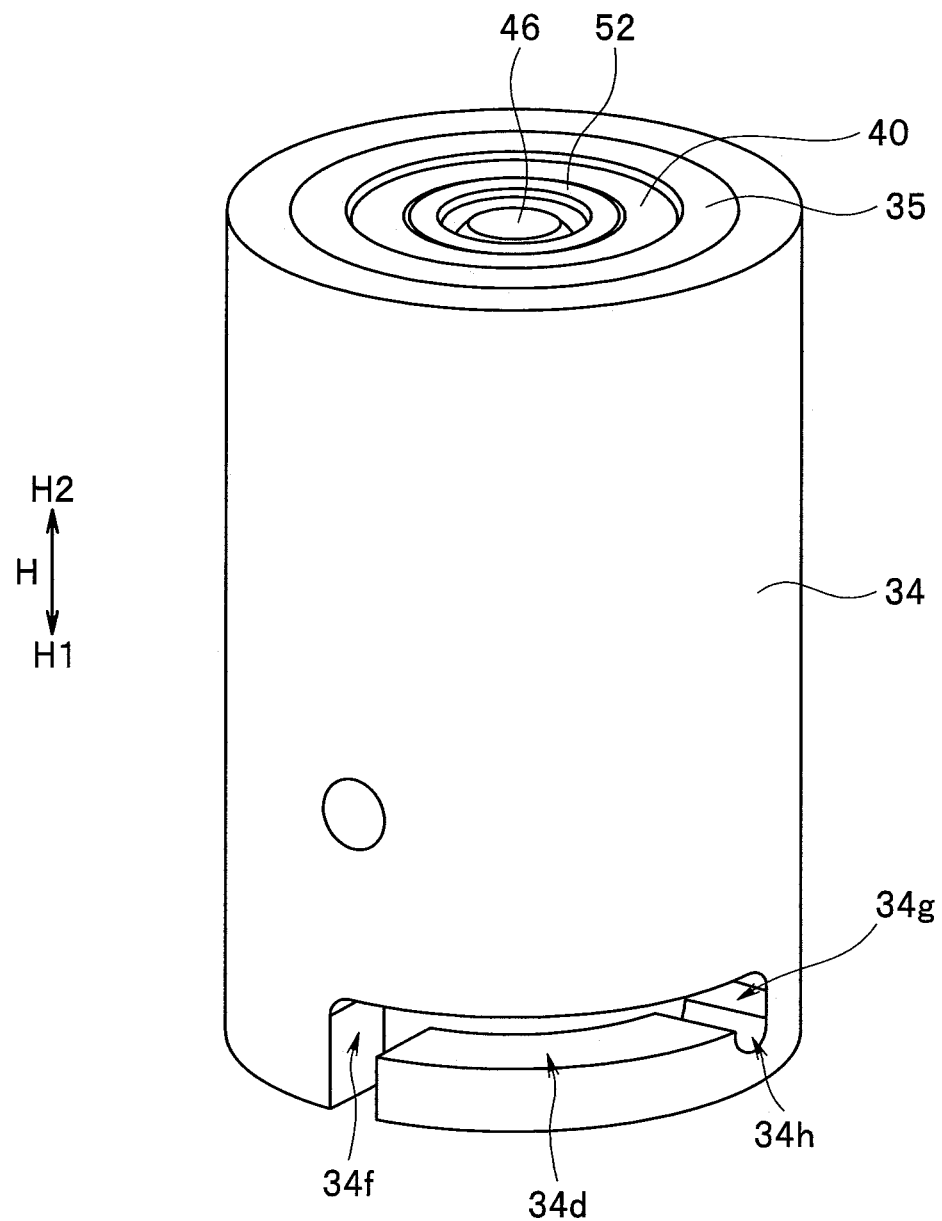
FIG. 11 is a perspective view of a sterilization adaptor that is attachable to and detachable from a vent pipe sleeve according to a second embodiment.
Figure 12:
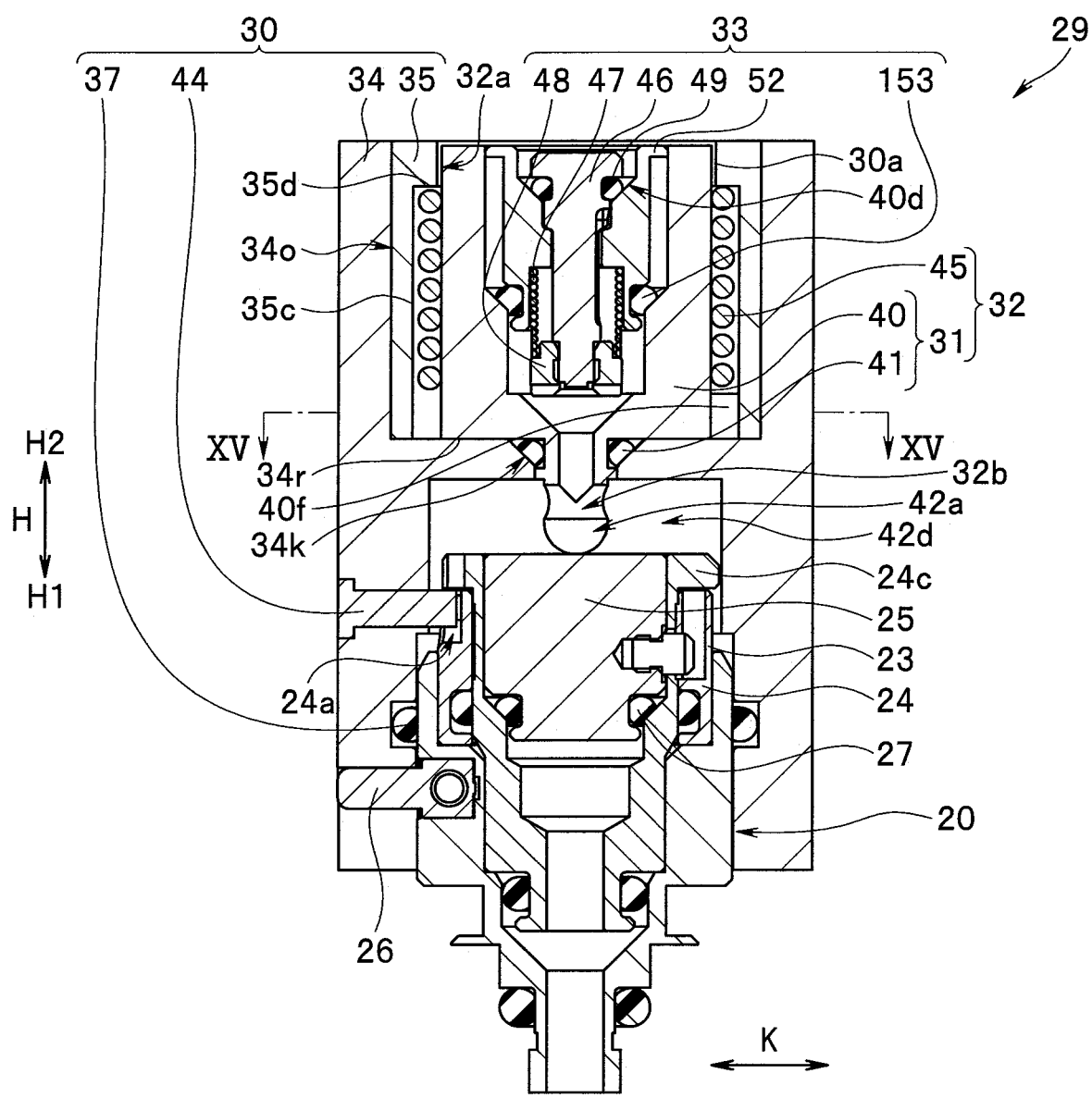
FIG. 12 is a sectional view illustrating a state where the sterilization adaptor illustrated in FIG. 11 is attached to the vent pipe sleeve and the guide pin is fitted into the first position of the guide groove formed in the sterilization adaptor.

FIG. 11 is a perspective view of a sterilization adaptor configured to be attachable to and detachable from a vent pipe sleeve according to the present embodiment. FIG. 12 is a sectional view illustrating a state where the sterilization adaptor illustrated in FIG. 11 is attached to the vent pipe sleeve and the guide pin is fitted into the first position of the guide groove formed in the sterilization adaptor.

Figure 13:
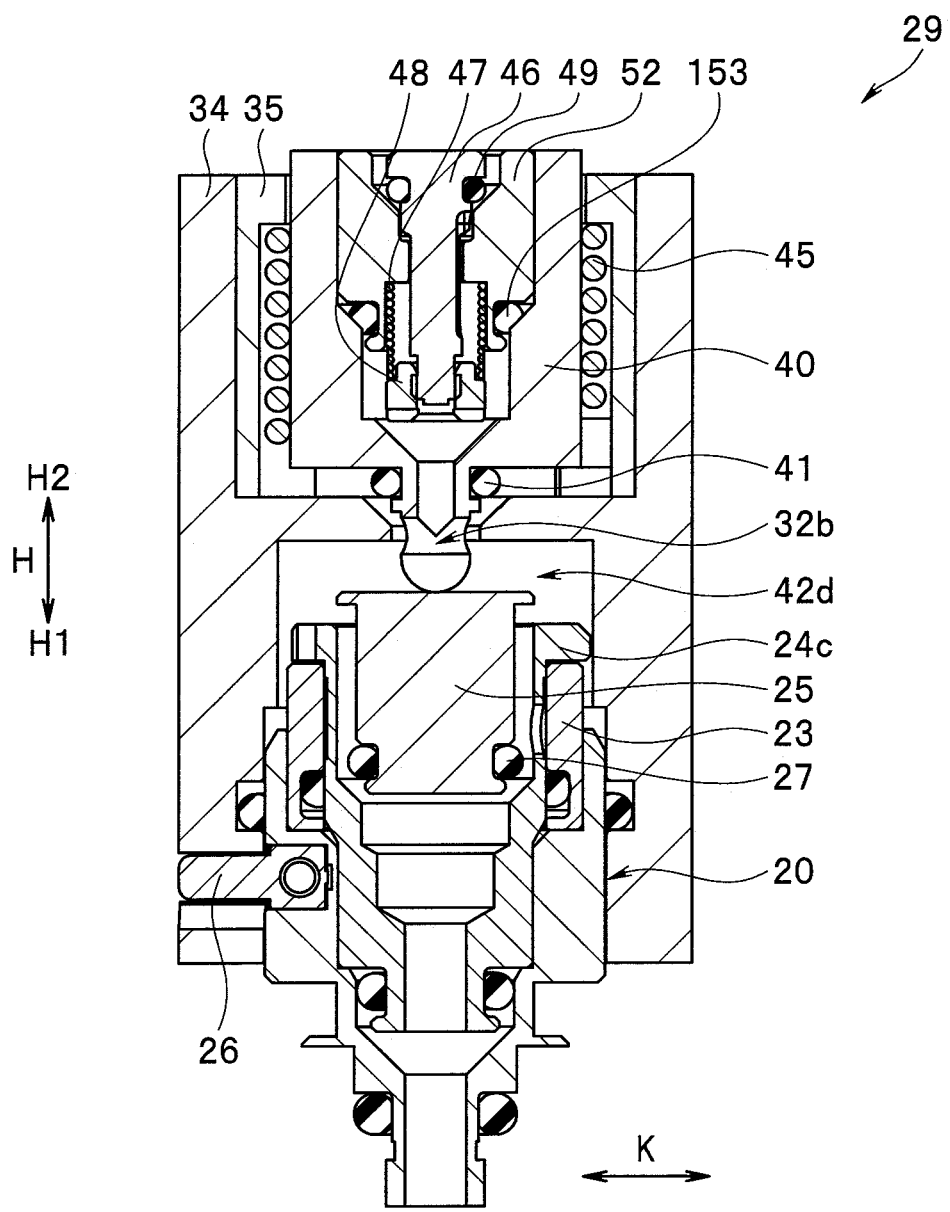
FIG. 13 is a sectional view of the vent pipe sleeve and the sterilization adaptor in a state where the guide pin illustrated in FIG. 12 is moved to the second position of the guide groove.
Figure 14:
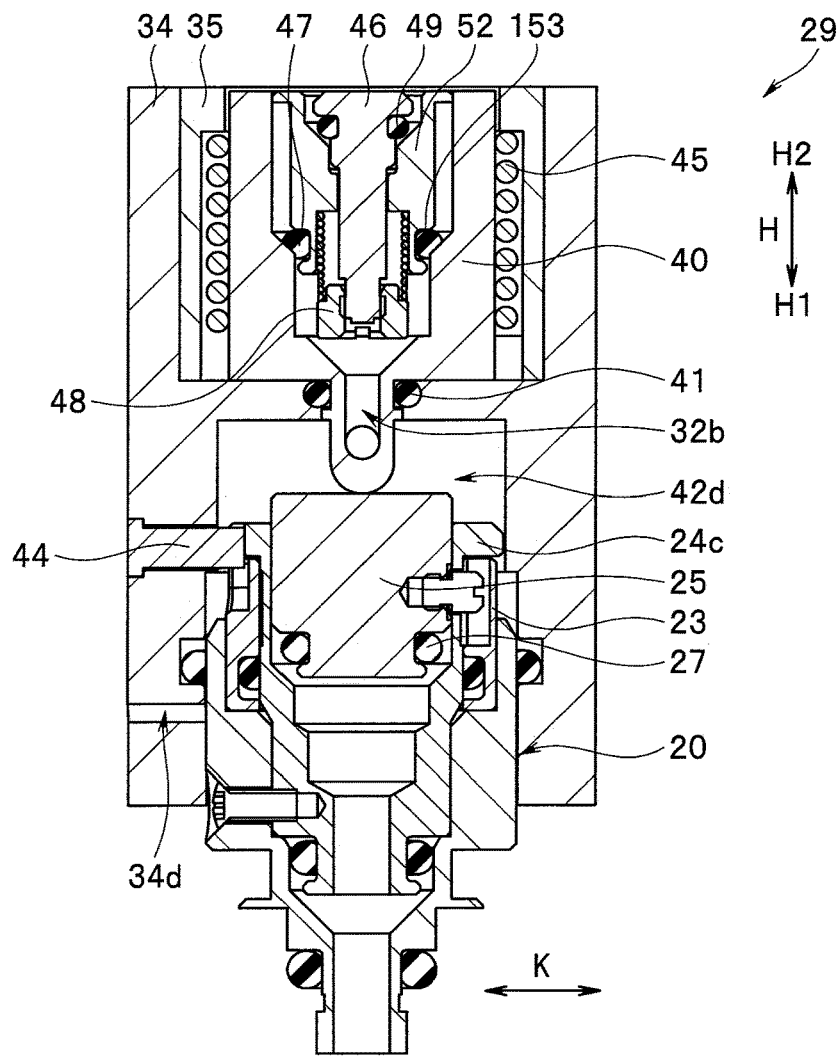
FIG. 14 is a sectional view of the vent pipe sleeve and the sterilization adaptor in a state where the guide pin illustrated in FIG. 13 is moved to the third position of the guide groove.

FIG. 13 is a sectional view of the vent pipe sleeve and the sterilization adaptor in a state where the guide pin illustrated in FIG. 12 is moved to the second position of the guide groove. FIG. 14 is a sectional view of the vent pipe sleeve and the sterilization adaptor in a state where the guide pin illustrated in FIG. 13 is moved to the third position of the guide groove.

Figure 15:
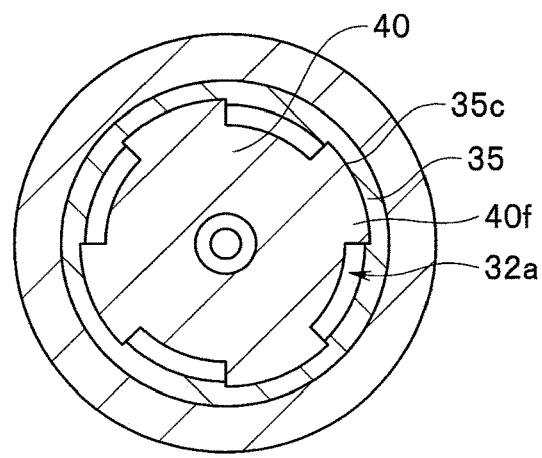
FIG. 15 is a sectional view of the sterilization adaptor taken along a line XV-XV in FIG. 12.
Figure 16:
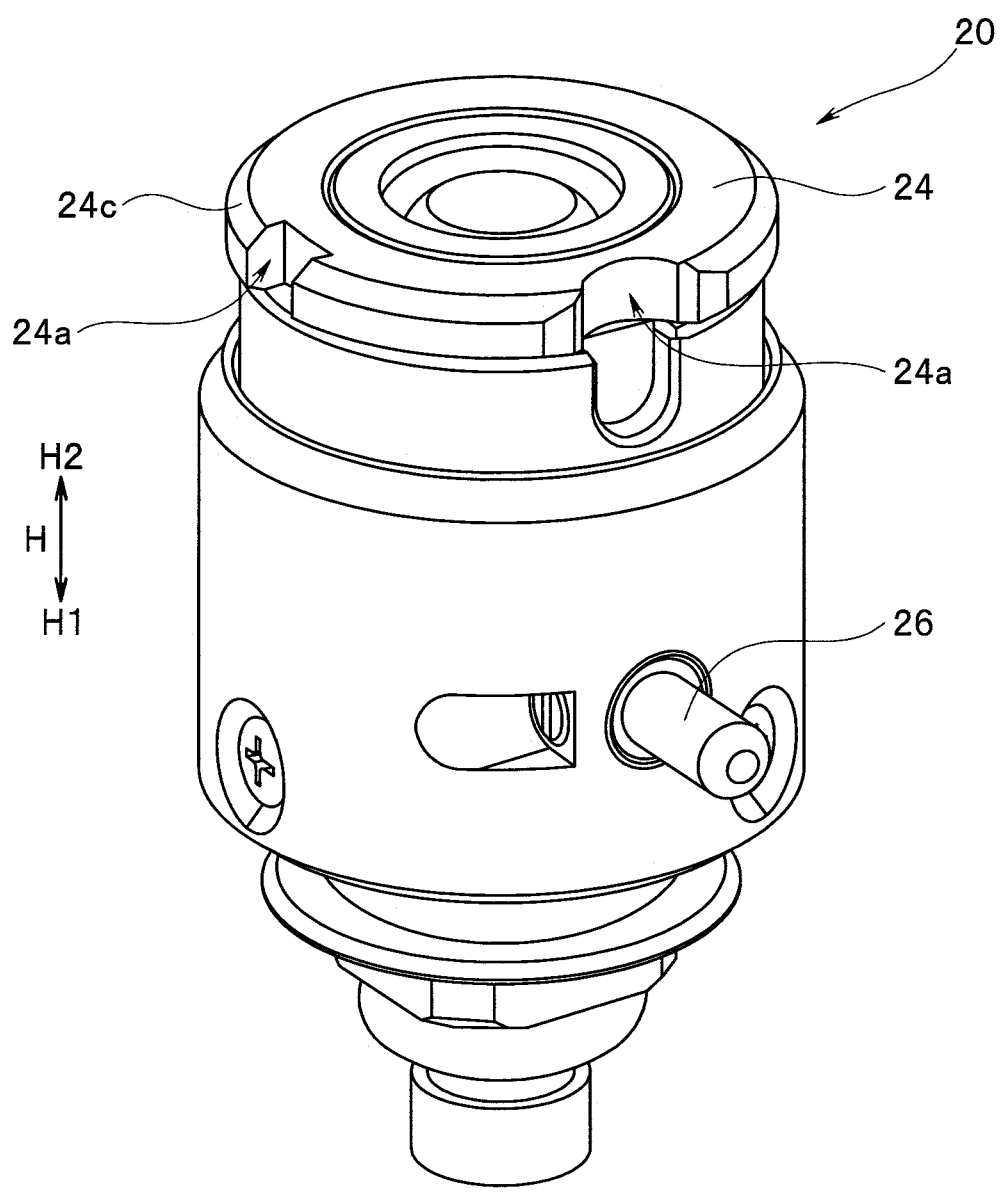
FIG. 16 is a perspective view of the vent pipe sleeve illustrated in FIG. 12.

Further, FIG. 15 is a sectional view of the sterilization adaptor taken along the line XV-XV in FIG. 12. FIG. 16 is a perspective view of the vent pipe sleeve illustrated in FIG. 12.

The configuration of the sterilization adaptor according to the second embodiment is different in the configuration of the vent valve unit from the sterilization adaptor according to the first embodiment illustrated in FIGS. 1 to 11 described above. Accordingly, only the difference will be described, and components similar to those of the first embodiment are denoted by the same reference numerals and the descriptions thereof are omitted.

As illustrated in FIG. 12, also in the present embodiment, the sterilization adaptor 29 includes a main part configured by the vent valve unit 32, the check valve unit 33, and the main body 30 like in the first embodiment described above.

The main body 30 includes a main part configured by the main body member 34, the spring pressing member 35, the cam pin 44, and the first seal member 37.

The main body member 34 is formed of a pipe-shaped member including a stepped portion on the inner peripheral surface.

Further, as illustrated in FIG. 11, the main body member 34 is provided with the guide groove 34d into which the guide pin 26 of the vent pipe sleeve 20 is fitted when the sterilization adaptor 29 is attached to the vent pipe sleeve 20, like in the first embodiment, on the outer peripheral surface in the section on the one end side H1 in the longitudinal axis direction H.

The cam pin 44 is provided on the main body member 34 along the radial direction K such that the distal end of the cam pin protrudes toward the inside of the main body member 34.

Further, the first seal member 37 is disposed in an annular groove formed on the inner peripheral surface of the main body member 34 in the section on the one end side H1 in the longitudinal axis direction H.

The spring pressing member 35 is formed of a pipe-shaped member with an inner peripheral surface formed in a stepped shape. A male screw formed on the outer peripheral surface of the spring pressing member is screwed and fixed into a female screw 34o formed on the inner peripheral surface of the main body member 34 in the section on the other end side H2 in the longitudinal axis direction H.

Further, four grooves 35c leading from an end portion on the one end side in the longitudinal axis direction H of the spring pressing member 35 to a stepped bottom surface 35d provided on the section on the other end side H2 in the longitudinal axis direction H are formed on the inner peripheral surface of the spring pressing member 35 at predetermined intervals in the peripheral direction of the spring pressing member 35 as illustrated in FIG. 15.

Further, the main body 30 includes inside thereof a bottom surface 34r formed along the radial direction K and the hole 30a formed along the longitudinal axis direction H. In the hole 30a, the vent valve unit 32 including the main part formed of the spring member 45 and the vent valve 31 is disposed.

The vent valve 31 includes a main part configured by the seal member 41 and the vent valve body 40.

Flange portions 40f are formed in the section on the one end side H1 in the longitudinal axis direction H of the vent valve body 40, and the gap 32a is formed between each of the flange portions 40f and the spring pressing member 35 as illustrated in FIG. 15.

The flange portions 40f are fitted into the respective grooves 35c of the spring pressing member 35. With this configuration, the vent valve body 40 is movable in the longitudinal axis direction with respect to the spring pressing member 35, and is formed to be integrally turnable in the peripheral direction.

Note that since the gap 32a is formed between each of the flange portions 40f and the spring pressing member 35, a part of each of the flange portions 40f may be formed into a D-cut shape. Further, the number of the flange portions 40f and the number of the grooves 35c are not limited to four, but instead a plurality of flange portions 40f and a plurality of grooves 35c may be provided.

The spring member 45 is disposed along the longitudinal axis direction H in a state where the spring member is contracted between the flange portions 40f and the stepped bottom surface 35d of the spring pressing member 35.

The main body member 34 is fixed to the outer peripheral surface of the vent pipe sleeve 20 by the first seal member 37.

In this state, the vent valve body 40 is moved to the one end side H1 in the longitudinal axis direction H by the biasing force of the spring member 45 toward the one end side H1 in the longitudinal axis direction H.

In addition, the seal member 41 is pressed against the tapered surface 34k formed on the bottom surface 34r of the main body member 34, thereby maintaining air-tightness between the main body member 34 and the vent valve body 40. In other words, the vent valve body 40 is closed.

The check valve unit 33 is disposed in the vent valve unit 32. The check valve unit 33 includes a main part configured by the shaft body 46, the spring member 47, the spring presser 48, the seal member 49, a valve body 52, and a seal member 153.

Note that the configuration of the check valve unit 33 is the same as that of the first embodiment, and the seal member 153 maintains air-tightness between the vent valve body 40 and the valve body 52.

Further, in order to allow the fluid passage 40d of the check valve unit 33 to communicate with the hole 30a between the main body 30 and the vent valve 31, the communication path 32b is formed in the protruding portion formed in the section on the one end side H1 in the longitudinal axis direction H of the vent valve body 40.

Note that as illustrated in FIG. 16, on the outer peripheral surface of the flange portion 24c of the sliding member 24 in the vent pipe sleeve 20, a groove 24a into which the cam pin 44 is fitted is formed at two positions, i.e., the position corresponding to the guide pin 26 in the peripheral direction and the position shifted in the peripheral direction by 90° from the position corresponding to the guide pin 26.

Note that the other configuration of the sterilization adaptor 29 is the same as that of the first embodiment described above.

Next, operations according to the present embodiment will be described.

When attaching the sterilization adaptor 29 to the vent pipe sleeve 20, the operator presses the main body member 34 toward the one end side H1 in the longitudinal axis direction H to cause the guide pin 26 of the vent pipe sleeve 20 to be fitted into the first position 34f of the guide groove 34d illustrated in FIG. 12, like in the first embodiment.

After that, the operator rotates to move the main body member 34 to the second position 34g of the guide groove 34d illustrated in FIG. 13, and then releases the grip to move the main body member 34 to the third position 34h of the guide groove 34d as illustrated in FIG. 14.

Note that in the case of rotating the main body member 34 from the first position 34f to the second position 34g, the main body member 34 is rotated in a state where the cam pin 44 is fitted into each of the grooves 24a.

With this configuration, the rotary ring 23 is rotated and the valve body 25 is moved to the other end side H2 in the longitudinal axis direction H along the cam groove formed in the sliding member 24, so that the seal member 27 is spaced apart from the tapered surface 24k and the vent pipe sleeve 20 is opened.

When the guide pin 26 is fitted into the third position 34h as illustrated in FIG. 2, the guide pin 26 is prevented from being detached due to the rotation of the sterilization adaptor 29 during the sterilization process.

When the pressure in the endoscope 2 becomes higher than the pressure in the sterilization apparatus during the sterilization process, like in the first embodiment described above, the shaft body 46 and the spring presser 48 are automatically lifted toward the other end side H2 in the longitudinal axis direction H against the biasing force of the spring member 47 toward the one end side H1 in the longitudinal axis direction H due to the difference in pressure, so that the seal member 49 is spaced apart from the tapered surface 40t. In other words, the check valve unit 33 is opened.

Accordingly, gas is discharged from the inside of the endoscope 2 into the sterilization apparatus through the gap between the sliding member 24 and the valve body 25 of the vent pipe sleeve 20, the space 42d in the main body 30, the communication path 32b, and the fluid passage 40d.

With this configuration, the pressure in the endoscope 2 is not higher than, or is equal to the pressure in the sterilization apparatus in the conditioning step. Accordingly, as described above, the bending rubber constituting the bending portion 8 can be prevented from being blown out.

After that, when gas is continuously discharged from the inside of the endoscope 2 into the sterilization apparatus and the difference between the pressure in the endoscope 2 and the pressure in the sterilization apparatus is lower than a prescribed pressure difference, the check valve unit 33 automatically closes due to the difference in pressure, so that the inside of the endoscope 2 and the inside of the sterilization apparatus are blocked from each other.

Accordingly, during the sterilization step, the inside of the endoscope 2 and the inside of the sterilization apparatus are blocked from each other, and thus sterilization gas is not introduced into the endoscope 2, thereby making it possible to prevent deterioration of internal members of the endoscope due to the gas.

In the case of removing the sterilization adaptor 29 from the vent pipe sleeve 20 after the completion of the sterilization step, when the operator depresses the main body member 34 against the biasing force of the spring member 45 toward the one end side H1 in the longitudinal axis direction H, the guide pin 26 is guided to the second position 34g, as illustrated in FIG. 13.

At this time, the protruding portion 42a is brought into contact with the valve body 25 of the vent pipe sleeve 20 and the seal member 41 is spaced apart from the tapered surface 34k against the biasing force of the spring member 45 toward the one end side H1 in the longitudinal axis direction H, so that the gap 32a is formed between the main body member 34 and the vent valve body 40 and the inside and the outside of the endoscope 2 communicate with each other. In other words, the vent valve body 40 is opened.

In this case, air enters into the endoscope 2 through the gap 32a, the space 42d, and the gap between the sliding member 24 and the valve body 25, so that the difference between the pressure in the endoscope 2 and the atmospheric pressure decreases.

Accordingly, it is possible to prevent the bending rubber constituting the bending portion 8 from being crimped to the plurality of bending pieces.

After that the operator grips the main body member 34 and rotates the main body member 34 in a direction opposite to that at the time of the attachment, and moves the guide pin 26 from the second position 34g illustrated in FIG. 13 to the first position 34f illustrated in FIG. 12.

As a result, when the rotary ring 23 is rotated in the direction opposite to that described above, the seal member 27 is brought into contact with the tapered surface 24k and thus the vent pipe sleeve 20 is closed.

After that, the main body member 34 is drawn out toward the other end side H2 in the longitudinal axis direction H, so that the guide pin 26 is removed from the guide groove 34d. As a result, the sterilization adaptor 29 is removed from the vent pipe sleeve 20.

Also, with this configuration, advantageous effects similar to those of the first embodiment described above can be obtained, and in the present embodiment, when the sterilization adaptor 29 is rotated and detached from the vent pipe sleeve 20 as described above, the protruding portion 42a contacts the valve body 25 at one point.

Accordingly, the frictional force between the vent pipe sleeve 20 and the protruding portion 42a at the time of rotation is smaller than that in the first embodiment, which enables the operator to detach the sterilization adaptor 29 with a small force.

Further, like in the first embodiment described above, in the case of attaching or detaching the sterilization adaptor 29, the main body 30 and the vent valve body 40 are rotated together.

Thus, it is possible to prevent the seal member 41 from being worn by a frictional force in the rotation direction to be repeatedly applied to the seal member 41 by the main body member and the valve body holding member being rotated separately.

Further, when the main body member 34 and the valve body holding member 42 are rotated separately, a force in the rotational direction is applied to the spring member 45 when attaching and detaching the sterilization adaptor.

However, when the main body member 34 and the valve body holding member 42 are rotated together like in the present embodiment, the force to be applied to the spring member can be reduced.

Accordingly, even when attachment and detachment are repeatedly performed, the spring member 45 and the seal member 41 are less likely to deteriorate and thus it is possible to prevent a failure from occurring in the sterilization adaptor 29.

Further, the configuration in which the spring pressing member 35 and the vent valve body 40 are screwed together has the same functions as the engaging pins 36 and the rotation prevention member 43 illustrated in the first embodiment described above.

Accordingly, advantageous effects similar to those of the first embodiment can also be obtained with a smaller number of components than in the first embodiment.

Third Embodiment

Figure 17:
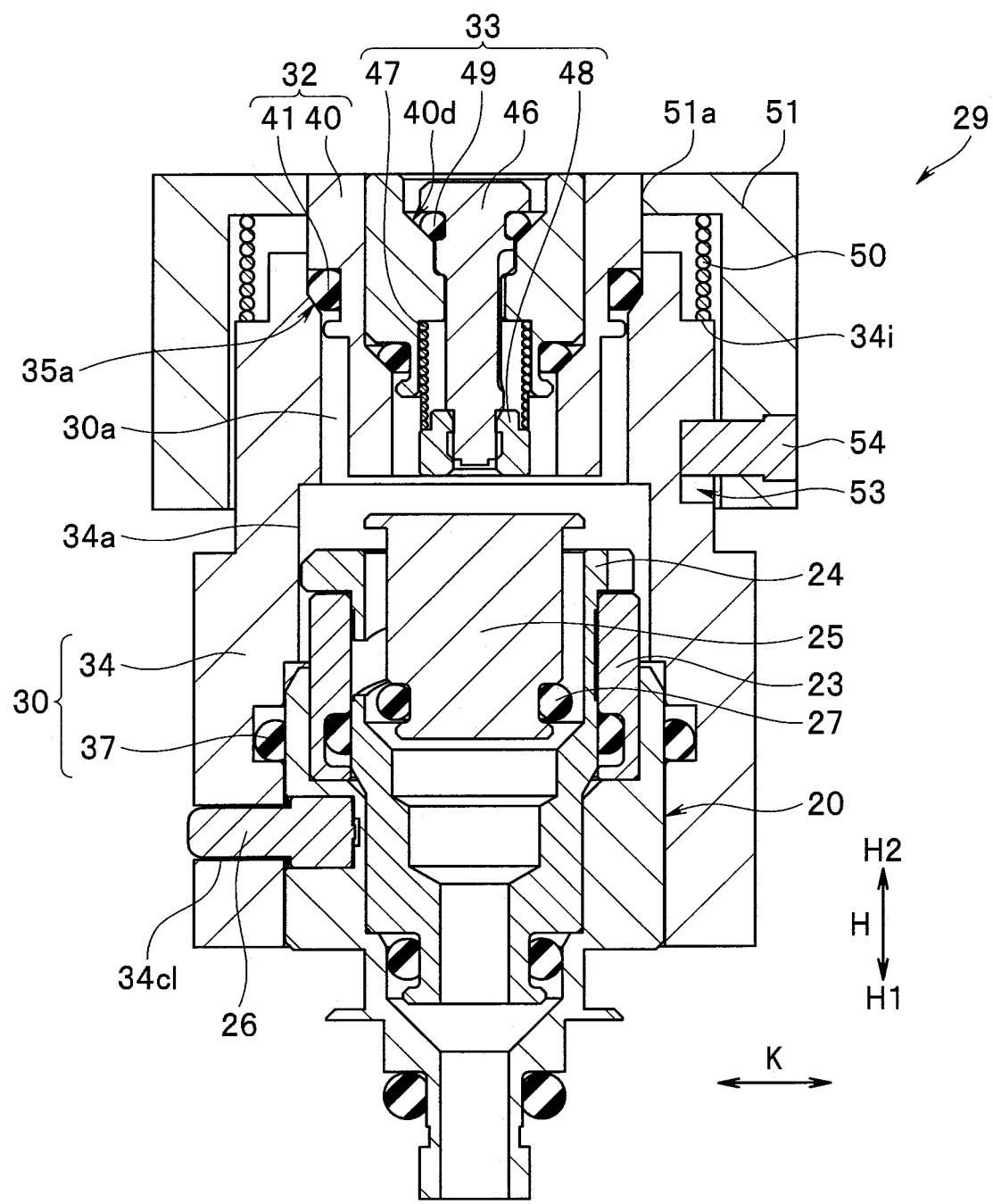
FIG. 17 is a sectional view illustrating a state where a sterilization adaptor according to a third embodiment is attached to a vent pipe sleeve.
Figure 18:
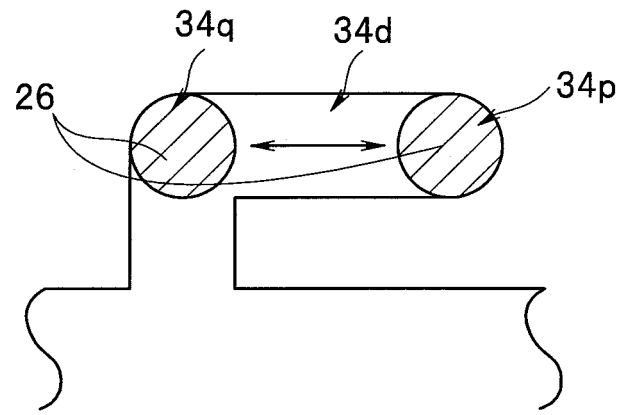
FIG. 18 is a diagram schematically illustrating a guide groove formed in a main body member of the sterilization adaptor illustrated in FIG. 17 and a guide pin provided on the vent pipe sleeve.
Figure 19:
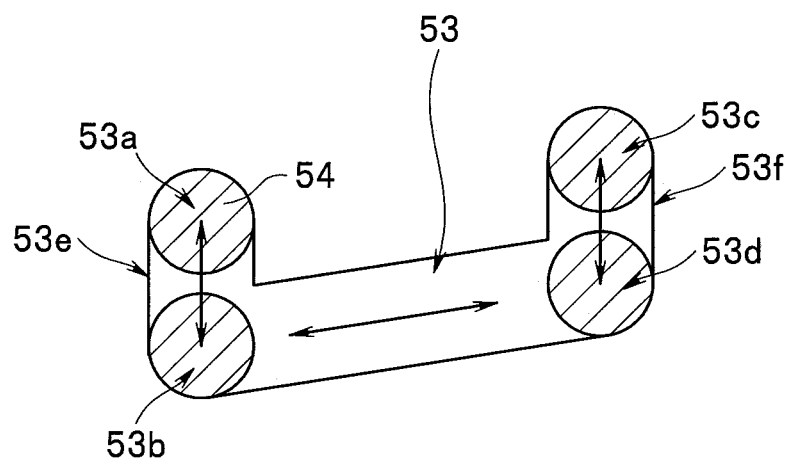
FIG. 19 is a diagram schematically illustrating a cam groove, which is formed in the main body member of the sterilization adaptor illustrated in FIG. 17 and is different from the cam groove illustrated in FIG. 18, and the cam pin provided on a grasping portion.

FIG. 17 is a sectional view illustrating a state where a sterilization adaptor according to the present embodiment is attached to the vent pipe sleeve. FIG. 18 is a diagram schematically illustrating the guide groove formed in the main body member of the sterilization adaptor illustrated in FIG. 17, and the guide pin provided on the vent pipe sleeve. FIG. 19 is a diagram schematically illustrating the cam groove which is different from the one illustrated in FIG. 18 and is formed in the main body member of the sterilization adaptor illustrated in FIG. 17, and the cam pin provided on the grasping portion.

Figure 20:
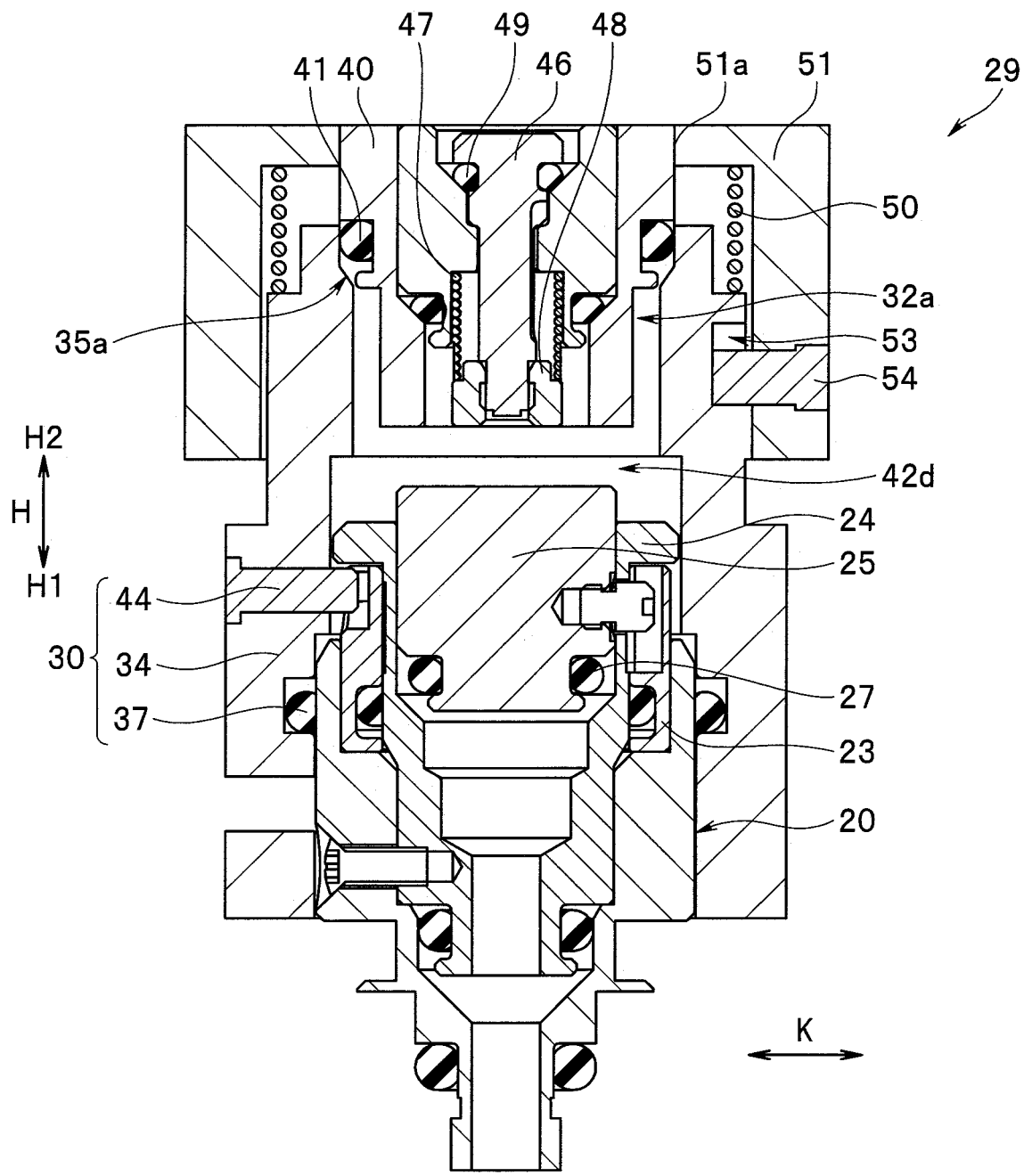
FIG. 20 is a sectional view of the vent pipe sleeve and the sterilization adaptor in a state where the vent valve body illustrated in FIG. 17 is opened.
Figure 21:
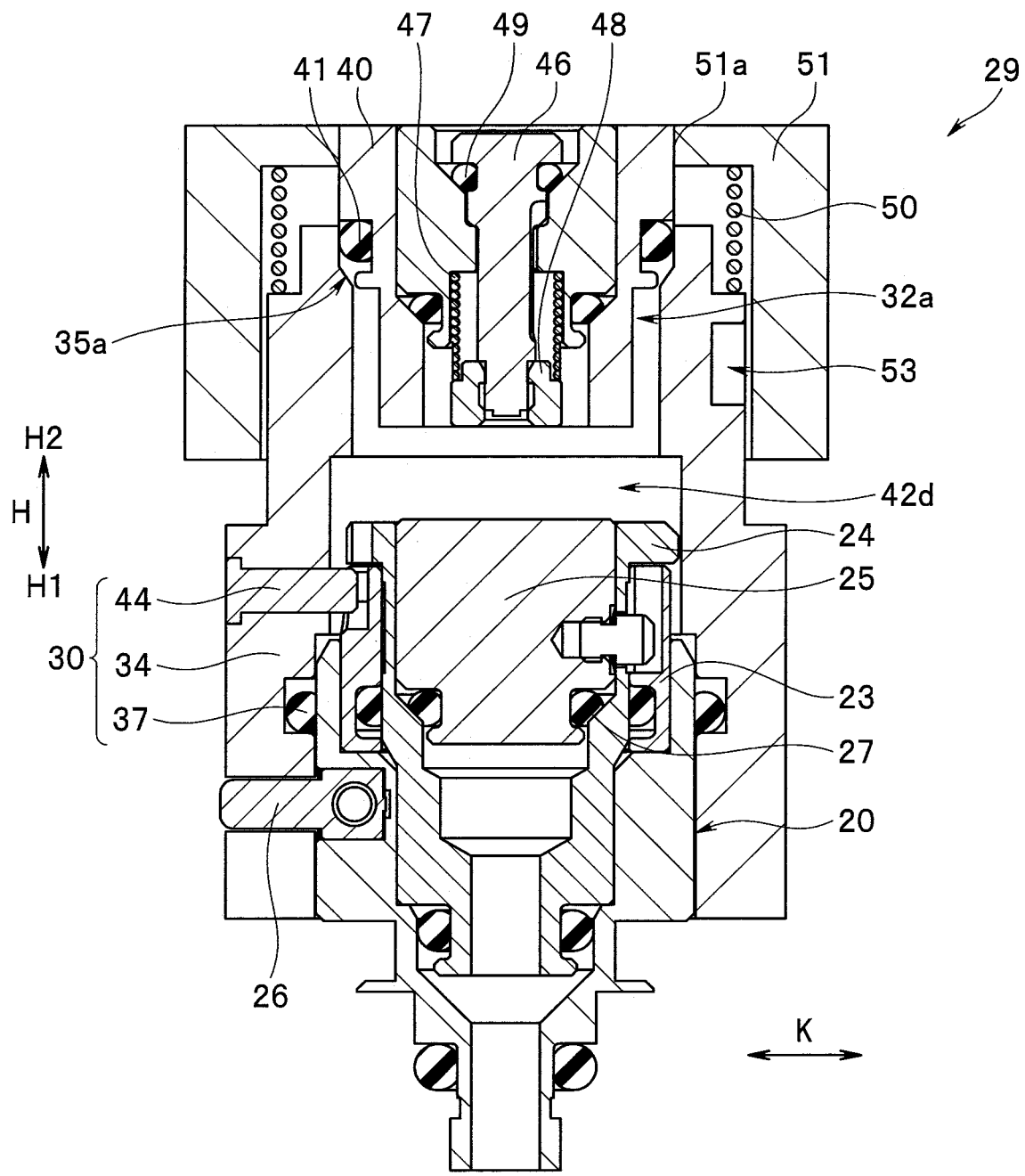
FIG. 21 is a sectional view of the vent pipe sleeve and the sterilization adaptor in a state where the vent pipe sleeve is closed from the state illustrated in FIG. 20.

FIG. 20 is a sectional view of the vent pipe sleeve and the sterilization adaptor in a state where the vent valve body illustrated in FIG. 17 is opened. FIG. 21 is a sectional view of the vent pipe sleeve and the sterilization adaptor in a state where the vent pipe sleeve is closed from the state illustrated in FIG. 20.

The configuration of the sterilization adaptor according to the third embodiment is different in the configuration of the vent valve unit, from the sterilization adaptor of the first embodiment illustrated in FIGS. 1 to 11 described above and the sterilization adaptor of the second embodiment illustrated in FIGS. 12 to 16. Accordingly, only the difference will be described, and components which are the same as those of the first and second embodiments are denoted by the same reference numerals and the descriptions thereof are omitted.

As illustrated in FIG. 17, in the present embodiment, the sterilization adaptor 29 includes a main part configured by the vent valve unit 32, the check valve unit 33, the main body 30, and a grasping portion 51.

Further, as illustrated in FIGS. 20 and 21, the main body 30 includes a main part configured by the main body member 34, the first seal member 37, and the cam pin 44.

The main body member 34 is formed of a pipe-shaped member in which the hole 30a, which is a stepped through-hole, is formed on the inner peripheral surface along the longitudinal axis direction H, and the tapered surface 35a is formed on the inner peripheral surface of the main body member.

Further, a groove is formed on the inner peripheral surface of the main body member 34 in the section on the one end side H1 in the longitudinal axis direction H, and the first seal member 37, such as an O-shaped ring, is disposed in the groove.

Further, the main body member 34 includes the guide groove 34d, as illustrated in FIG. 18, formed in the section on the one end side H1 in the longitudinal axis direction H with respect to the groove in which the first seal member 37 is disposed, and a guide groove 53 illustrated in FIG. 19 is formed in the section on the other end side H2 in the longitudinal axis direction H.

Further, in the main body member 34, the cam pin 44 is provided along the radial direction K such that the distal end of the cam pin protrudes toward the hole 30a at the same position as the position illustrated in the second embodiment described above.

The grasping portion 51 is formed in a pipe shape including an inward flange in the section on the other end side H2 in the longitudinal axis direction H, and a pin 54 is disposed in a hole penetrating through in the radial direction K in the section on the one end side H1 in the longitudinal axis direction H such that the pin protrudes toward the inside the grasping portion 51.

The pin 54 is engageable with the guide groove 53 as illustrated in FIG. 19, and is slidable to positions 53a to 53c along the guide groove 53.

The vent valve unit 32 includes a main part configured by the vent valve body 40 and the seal member 41.

The vent valve body 40 is formed of a pipe-shaped member, and includes, on the groove formed on the outer peripheral surface thereof, the seal member 41 such as an O-shaped ring.

Further, the vent valve body 40 is fixed by bonding to a hole 51a in a hole of the inward flange portion provided on the grasping portion 51. Such a configuration enables the vent valve body 40 to move and rotate integrally with the grasping portion 51.

A spring member 50 is disposed so as to be contracted between a recessed portion 34i formed on an end face on the other end side H2 in the longitudinal axis direction H of the main body member 34 in the longitudinal axis direction H and the inward flange portion of the grasping portion 51.

When the operator releases the grip of the grasping portion 51, the spring member 50 causes the pin 54 to be fitted into the positions 53a and 53c illustrated in FIG. 19.

Further, as illustrated in FIGS. 20 and 21, when the operator rotates the grasping portion 51 in the axial direction, the vent valve body 40 is lifted toward the one end side H2 in the longitudinal axis direction H and the pin 54 is moved to a position 53d illustrated in FIG. 19. When the seal member 41 is separated from the tapered surface 35a, the gap 32a is formed between the main body member 34 and the vent valve body 40, and between the main body member 34 and the grasping portion 51. In other words, the vent valve body 40 is opened.

In the state where the vent pipe sleeve 20 is opened, the gap 32a causes the inside of the endoscope 2 to communicate with the outside of the endoscope 2.

Note that the check valve unit 33 has the same structure as that of the second embodiment described above, and is disposed in the vent valve body 40 in the vent valve unit 32.

Further, in the present embodiment, the fluid passage 40d in the vent valve unit 32 and the hole 30a communicate with each other through the space 42d in the main body member 34.

Note that the other configurations are the same as those in the first and second embodiments described above.

Next, operations according to the present embodiment will be described.

When the sterilization adaptor 29 is attached to the vent pipe sleeve 20, first the operator presses the sterilization adaptor 29 against the vent pipe sleeve 20 toward the one end side H1 in the longitudinal axis direction H until the guide pin 26 is guided to a position 34q in the guide groove 34d illustrated in FIG. 18.

As a result, the grasping portion 51 is also moved to the one end side H1 in the longitudinal axis direction H, and the pin 54 is moved from the position 53c to the position 53d in the guide groove 53 illustrated in FIG. 19. In this case, as illustrated in FIG. 20, the vent valve unit 32 is opened.

After that, when the operator rotates the grasping portion 51 in a state where the pin 54 is located at the position 53d, the grasping portion 51, the vent valve unit 32, and the check valve unit 33 are integrally moved to the one end side H1 in the longitudinal axis direction H.

As a result, the seal member 41 is pressed against the tapered surface and the vent valve unit is closed.

After that, when the rotation is continued, the pin 54 is hooked at one end portion 53e of the guide groove 53 and the pin 54 is moved to the position 53b.

At this time, the main body member 34 is integrally rotated with the grasping portion 51, so that the guide pin 26 is guided to a position 34p in the guide groove 34d illustrated in FIG. 18 and thus the vent pipe sleeve 20 is opened.

After that, when the operator releases the grip of the sterilization adaptor 29, the pin 54 is moved to the position 53a in the guide groove 34d. In this state, the sterilization process is performed.

That is, in the present embodiment, the sterilization adaptor 29 is attached in two stages in which the grasping portion 51 is rotated and thereafter the main body member 34 is rotated.

During the sterilization process, similarly as in the second embodiment described above, when the pressure in the endoscope 2 becomes higher than the pressure in the sterilization apparatus by the check valve unit 33, gas is discharged from the inside of the endoscope 2 into the sterilization apparatus. This configuration prevents the bending rubber constituting the bending portion 8 from being blown out.

Further, the sterilization adaptor 29 engages with the guide groove 53 at a depth where the pin 54 can be easily hooked by the biasing force of the spring member 50 toward the one end side H1 in the longitudinal axis direction H, thereby preventing the grasping portion 51 from being rotated and detached during the sterilization process.

This configuration can prevent a situation where the vent valve body 40 is opened during the sterilization process and gas enters into the endoscope 2 and deteriorates the components.

After the sterilization process, when the sterilization adaptor 29 is detached from the vent pipe sleeve 20, the operator first presses the grasping portion 51 into the one end side H1 in the longitudinal axis direction H against the biasing force of the spring member 50 toward the one end side H1 in the longitudinal axis direction H.

In this case, the pin 54 is moved from the position 53a to the position 53b in the guide groove 53. After that, when the grasping portion 51 is rotated along the guide groove 53 in the direction opposite to that at the time of attachment, the pin 54 is moved to the position 53d.

In this case, when the pin 54 is moved from the position 53a to the position 53b and then to the position 53d in the guide groove 53, the vent valve body 40 is moved to the other end side H2 in the longitudinal axis direction H and the seal member 41 is separated from the tapered surface 35a as illustrated in FIG. 20, so that a gap is formed between the main body member 34 and the vent valve body 40.

In this case, the pressure in the endoscope 2 is a negative pressure, and thus air flows into the endoscope 2 through the gap 32a, the space 42d, and the gap between the valve body 25 and the sliding member 24 of the vent pipe sleeve 20.

Accordingly, in the present embodiment, the vent valve body 40 can be reliably opened before the vent pipe sleeve 20 starts to be closed when the sterilization adaptor 29 is detached, thereby making it possible to reliably release the negative pressure state in the endoscope 2.

Therefore, it is possible to prevent the bending rubber constituting the bending portion 8 from biting into the plurality of bending pieces and being damaged by the bending portion 8 being used in a state where the bending rubber is crimped to the plurality of bending pieces.

Further, when the operator presses the grasping portion 51 by the biasing force of the spring member 50, a click sensing can be obtained. This makes it possible to reliably check whether the vent valve body 40 is opened.

When the main body 30 is further rotated from the state where the pin 54 is at the position 53d, the pin 54 is hooked at another end portion 53f of the guide groove 53. This causes the main body member 34 to rotate following the grasping portion 51.

At this time, as illustrated in FIG. 18, the guide pin 26 is moved to the position 34q in the guide groove 34d.

As a result, as illustrated in FIG. 21, the valve body 25 of the vent pipe sleeve 20 is moved to the one end side H1 in the longitudinal axis direction H by the cam pin 44, so that the seal member 27 contacts the tapered surface 24k and the vent pipe sleeve 20 is closed.

Such a configuration can also provide advantageous effects similar to those of the first and second embodiments described above.

Note that the first to third embodiments are described by taking an endoscope as an example of a medical device. However, the medical device is not limited to an endoscope. The present invention is also applicable to medical devices provided with a vent pipe sleeve, other than an endoscope.

The present invention is not limited to the above-described embodiments, but can be changed as appropriate in a range without departing from the gist or thought of the invention as read from the appended claims and throughout the specification, and also an insertion instrument and an endoscope with such changes are included in the technical range of the present invention.

What is claimed is:

1. A sterilization adaptor configured to be attachable to and detachable from a medical device, the sterilization adaptor comprising:
   a check valve unit for inhibiting circulation of gas from an outside of the medical device to an inside of the medical device when the sterilization adaptor is attached to the medical device, and for circulating the gas from the inside to the outside;
   a main body including a hole; and
   a vent valve unit disposed in the hole, the vent valve unit causing the inside and the outside to communicate with each other through a gap formed between the vent valve unit and the main body and blocking the gap,
   wherein the check valve unit is disposed in the vent valve unit;
   the check valve unit includes a fluid passage for circulating the gas; and
   the vent valve unit includes a communication path for causing the gap to communicate with the fluid passage,
   wherein the vent valve unit includes:
   a vent valve in which the check valve unit is disposed;
   a vent valve holding member coupled to the vent valve and provided with the communication path;
   a rotation prevention member coupled to the vent valve holding member and configured to prevent rotation of the main body relative to the vent valve; and
   an elastic member disposed so as to couple the main body and the rotation prevention member and configured to bias the vent valve in a predetermined direction through the vent valve holding member and the rotation prevention member to block the gap, and
   wherein the main body includes an engaging portion configured to be engageable with the medical device by a biasing force of the elastic member.

2. A sterilization adaptor configured to be attachable to and detachable from a medical device, the sterilization adaptor comprising:
   a check valve unit for inhibiting circulation of gas from an outside of the medical device to an inside of the medical device when the sterilization adaptor is attached to the medical device, and for circulating the gas from the inside to the outside;
   a main body including a hole; and
   a vent valve unit disposed in the hole, the vent valve unit causing the inside and the outside to communicate with each other through a gap formed between the vent valve unit and the main body and blocking the gap,
   wherein the check valve unit is disposed in the vent valve unit;
   the check valve unit includes a fluid passage for circulating the gas; and
   the vent valve unit includes a communication path for causing the gap to communicate with the fluid passage,
   wherein the vent valve unit includes:
   a vent valve in which the check valve unit is disposed;
   a vent valve holding member coupled to the vent valve and provided with the communication path;
   a rotation prevention member coupled to the vent valve holding member and configured to prevent rotation of the main body relative to the vent valve; and
   an elastic member disposed so as to couple the main body and the rotation prevention member and configured to bias the vent valve in a predetermined direction through the vent valve holding member and the rotation prevention member to block the gap, and
   wherein blocking of the gap is released by moving the vent valve through the vent valve holding member by pressing the medical device against a biasing force of the elastic member.

* * * * *